US012790319B2

(12) United States Patent
Lin et al.

(10) Patent No.: US 12,790,319 B2
(45) Date of Patent: Nov. 10, 2026

(54) CELL-PERMEANT COVALENT INHIBITORS OF VIRAL CYSTEINE PROTEASES

(71) Applicants: THE BOARD OF TRUSTEES OF THE LELAND STANFORD JUNIOR UNIVERSITY, Stanford, CA (US); AARHUS UNIVERSITY, Aarhus C (DK)

(72) Inventors: Michael Z. Lin, Stanford, CA (US); Michael Westberg Soerensen, Stanford, CA (US)

(73) Assignees: THE BOARD OF TRUSTEES OF THE LELAND STANFORD JUNIOR UNIVERSITY, Stanford, CA (US); AARHUS UNIVERSITY, Aarhus C (DK)

( * ) Notice: Subject to any disclaimer, the term of this patent is extended or adjusted under 35 U.S.C. 154(b) by 273 days.

(21) Appl. No.: 18/777,100

(22) Filed: Jul. 18, 2024

(65) Prior Publication Data

US 2026/0022111 A1 Jan. 22, 2026

(51) Int. Cl.

| | |
|---|---|
| ***C07D 403/14*** | (2006.01) |
| ***A61K 31/4025*** | (2006.01) |
| ***A61K 31/403*** | (2006.01) |
| ***A61K 45/06*** | (2006.01) |

(52) U.S. Cl.

CPC ........ *C07D 403/14* (2013.01); *A61K 31/4025* (2013.01); *A61K 31/403* (2013.01); *A61K 45/06* (2013.01)

(58) Field of Classification Search

CPC .................................................... C07D 403/14

See application file for complete search history.

(56) References Cited

U.S. PATENT DOCUMENTS

2018/0267722 A1 9/2018 Emma et al.

FOREIGN PATENT DOCUMENTS

WO WO-2021/226546 A1 11/2021

OTHER PUBLICATIONS

International Patent Application No. PCT/US2022/053248, International Search Report and Written Opinion, dated Mar. 31, 2023.

Janin, On the origins of SARS-CoV-2 main protease inhibitors, RSC Med.Chem., 15(7):81-118 (2024).

PubChem, SID 228237079, Feb. 12, 2015.

PubChem, SID 228709927, Feb. 12, 2015.

PubChem, SID 233671287, Feb. 12, 2015.

PubChem, SID 237655117, Feb. 13, 2015.

PubChem, SID 377105436, Dec. 15, 2018.

PubChem, SID 56338202, Oct. 27, 2008.

*Primary Examiner* — Golam M Shameem

(74) *Attorney, Agent, or Firm* — MARSHALL, GERSTEIN & BORUN LLP

(57) ABSTRACT

Provided herein are compounds having a structure of formula (I) or formula (II):

(I)

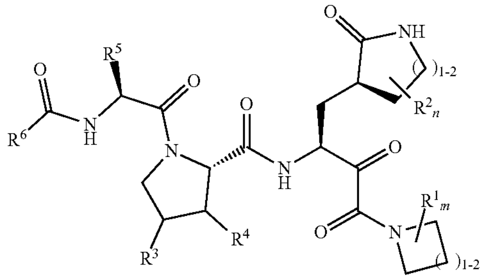

or (II)

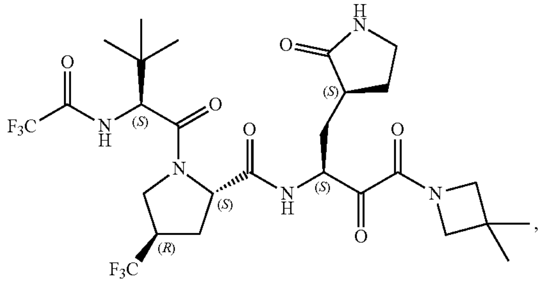

or a pharmaceutically acceptable salt, solvate, or hydrate thereof, useful in treating or preventing coronavirus infection. In some embodiments, the coronavirus infection is COVID-19 (SARS-CoV-19). Also provided are compositions comprising the compounds, as well methods of using the compounds to treat or prevent coronavirus infection.

27 Claims, No Drawings

CELL-PERMEANT COVALENT INHIBITORS OF VIRAL CYSTEINE PROTEASES

This invention was made with Government support under contract AI171421 awarded by the National Institutes of Health. The Government has certain rights in the invention.

BACKGROUND

Viral infections represent a major cause of disease worldwide. For example, the novel coronavirus (CoV), Severe Acute Respiratory Syndrome Coronavirus 2 (SARS-CoV-2), was first identified in December 2019 as the cause of a respiratory illness designated coronavirus disease 2019, or COVID-19. COVID-19 is characterized by respiratory symptoms with varying degrees of severity, from mild upper respiratory illness to severe interstitial pneumonia and acute respiratory distress syndrome, aggravated by thrombosis in the pulmonary microcirculation. Its clinical evolution is characterized by three main phases—early infection phase, pulmonary phase, and hyperinflammation phase—with clinical features ranging from mild or no symptoms to acute respiratory distress syndrome and multi-organ failure.

SARS-CoV-2 is a positive-sense single-stranded RNA virus that belongs to the β-coronavirus family along with SARS and MERS. The CoV main protease ($M^{pro}$) is a recognized major target for antiviral drugs. $M^{pro}$ is a 3-chymotrypsin-like protease with a catalytic cysteine residue. $M^{pro}$ processes the viral polyprotein into separate proteins in an early step of the CoV life cycle, and its activity is required for viral replication. Prior to the emergence of SARS-CoV-2, experimental inhibitors of $M^{pro}$ were found to protect mice and cats from lethal CoV diseases. The SARS-CoV-2 $M^{pro}$ inhibitor nirmatrelvir (NTV) reduced hospitalization risk by 79% in unvaccinated COVID-19 patients, leading to its emergency approval in multiple countries. A non-covalent non-peptidomimetic $M^{pro}$ inhibitor, ensitrelvir (ETV) has also shown clinical efficacy and been approved for emergency use in Japan. In China, Simnotrelvir, Leritrelvir (RAY1216), and Atilotrelvir have been conditionally approved. Additional oral $M^{pro}$ inhibitors that are currently or have been tested in clinical trials include pomotrelvir (PTV), EDP-235, ALG-097558, and HS-10517 (GDDI-4405). While a range of $M^{pro}$-targeted SARS-CoV-2 therapies now exist or are in development, there remains a need for diverse and effective $M^{pro}$-targeted therapeutics for treatment of CoV (e.g., SARS-CoV-2) infections, including but not limited to COVID-19.

In view of the foregoing, there remains a need for compounds for treating or preventing viral infections, including coronavirus infections.

SUMMARY

Provided herein are compounds having a structure of formula (I) or formula (II):

(I)

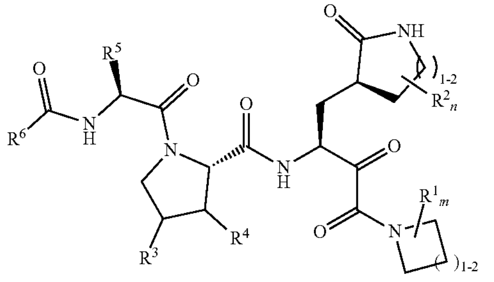

or

-continued (II)

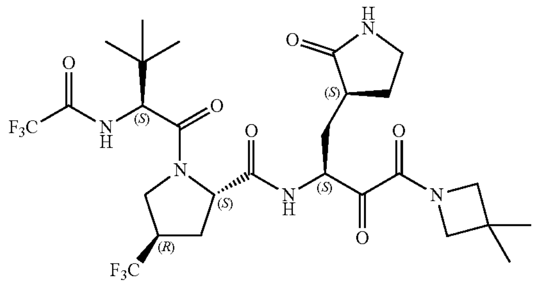

, or a pharmaceutically acceptable salt, solvate, or hydrate thereof, wherein $R^1$ and $R^2$ are each independently halo, $C_{1-3}$alkyl, or halo$C_{1-3}$alkyl;

m and n are each independently 0, 1, or 2;

$R^3$ and $R^4$ are each independently H, $C_{1-3}$alkyl, halo$C_{1-3}$ alkyl, or a 3 to 6-membered spiro ring optionally comprising 1 or 2 ring heteroatoms independently selected from N, O, and S, and the spiro ring is substituted with 0-2 $R^a$, or $R^3$ and $R^4$, taken together with the carbon atoms to which they are attached, form a $C_{3-6}$cycloalkyl substituted with 0-2 $R^a$;

each $R^a$ is independently halo, $C_{1-3}$alkyl, or halo$C_{1-3}$ alkyl;

$R^5$ is $C_{1-3}$alkyl, isobutyl, bridged bicyclo$C_{5-8}$alkyl, alkylene-$C_{3-8}$cycloalkyl, alkylene-$C_{1-4}$alkoxy, alkylene-O—$C_{3-8}$cycloalkyl wherein the cycloalkyl is optionally substituted with $C_{1-3}$alkyl; or $C_{3-8}$cycloalkyl optionally substituted with $C_{1-3}$alkyl, halo, halo$C_{1-4}$ alkyl, or $C_{1-3}$alkoxy; and $R^6$ is $C_{1-3}$alkyl, halo$C_{1-6}$-alkyl, $C_{1-4}$alkoxy, $C_{3-6}$cycloalkoxy, or -haloalkylene-$C_{3-6}$-cycloalkyl.

In some embodiments, the disclosure provides pharmaceutical compositions and kits comprising the disclosed compounds, as well as methods of using the disclosed compounds.

DETAILED DESCRIPTION

The present disclosure provides covalent protease inhibitor compounds that find use in inhibiting viral protease activity (e.g., coronavirus viral protease activity, such as SARS-CoV-2 main protease activity). In turn, the compounds find use in inhibiting viral replication for, e.g., treating and/or preventing a coronavirus infection in an individual in need thereof.

The disclosure provides a compound having a structure of formula (I) or formula (II):

(I)

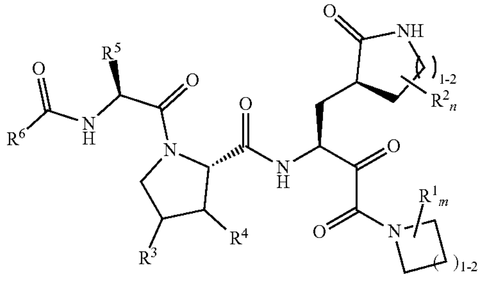

or

-continued (II)

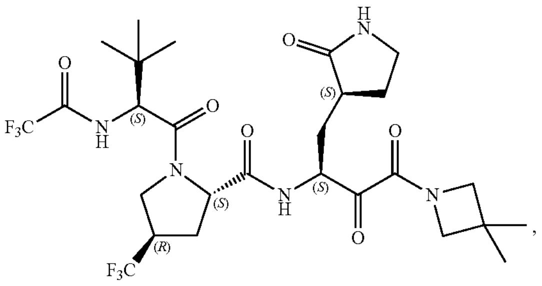

as described herein.

In some embodiments, the disclosure provides a pharmaceutically acceptable salt, solvate, or hydrate thereof of the disclosed compounds.

Any assignments of absolute(S)/(R) stereochemical configurations of chiral centers are intended to be given in relation to the final compounds where all R groups have been fully expanded. In case of ambiguity between the name and a drawn structure, the structure controls.

The phrase "pharmaceutically acceptable salts", as used herein, unless otherwise indicated, includes salts of acidic or basic groups which may be present in the compounds described herein. The compounds of the present disclosure that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as but not limited to the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, hexylresorcinate, hydrabamine, hydrobromide, hydrochloride, iodide, isethionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts. Additionally, the salts of the compounds described herein, can exist in either hydrated or anhydrous form or as solvates with other solvent molecules.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this disclosure. Such compounds are useful, for example, as analytical tools or probes in biological assays. Such compounds, especially deuterium analogs, can also be therapeutically useful. Thus, further disclosed herein are deuterated compounds or salts of formula (I) or formula (II), in which one or more isotopes of hydrogen have been replaced with deuterium.

The compounds of the disclosure are defined herein by their chemical structures and/or chemical names. Where a compound is referred to by both a chemical structure and a chemical name, and the chemical structure and chemical name conflict, the chemical structure is determinative of the compound's identity.

Compounds of Formula (I)

In some embodiments, the disclosure provides compounds having a structure of formula (I), (I)

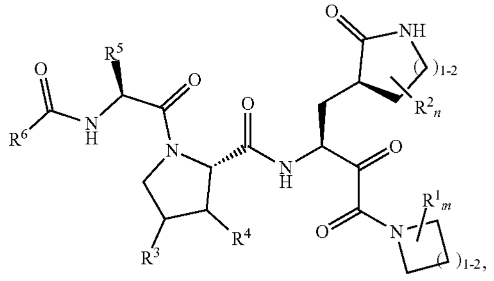

or a pharmaceutically acceptable salt, solvate, or hydrate thereof, wherein $R^1$ and $R^2$ are each independently halo, $C_{1-3}$alkyl, or halo$C_{1-3}$alkyl;

m and n are each independently 0, 1, or 2;

$R^3$ and $R^4$ are each independently H, $C_{1-3}$alkyl, halo$C_{1-3}$ alkyl, or a 3 to 6-membered spiro ring optionally comprising 1 or 2 ring heteroatoms independently selected from N, O, and S, and the spiro ring is substituted with 0-2 $R^a$, or $R^3$ and $R^4$, taken together with the carbon atoms to which they are attached, form a $C_{3-6}$cycloalkyl substituted with 0-2 $R^a$;

each $R^a$ is independently halo, $C_{1-3}$alkyl, or halo$C_{1-3}$ alkyl;

$R^5$ is $C_{1-3}$alkyl, isobutyl, bridged bicyclo$C_{5-8}$alkyl, alkylene-$C_{3-8}$cycloalkyl, alkylene-$C_{1-4}$alkoxy, alkylene-O—$C_{3-8}$cycloalkyl wherein the cycloalkyl is optionally substituted with $C_{1-3}$alkyl; or $C_{3-8}$cycloalkyl optionally substituted with $C_{1-3}$alkyl, halo, halo$C_{1-4}$ alkyl, or $C_{1-3}$alkoxy; and $R^6$ is $C_{1-3}$alkyl, halo$C_{1-6}$alkyl, $C_{1-4}$alkoxy, $C_{3-6}$cycloalkoxy, or -haloalkylene-$C_{3-6}$cycloalkyl.

Chemical Definitions

As used herein, "halo" or "halogen" refers to —F (fluoro), —Cl (chloro), —Br (bromo), or —I (iodo).

As used herein, "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-8}$alkyl refers to an alkyl group having a number of carbon atoms encompassing the entire range (e.g., 1 to 8 carbon atoms), as well as all subgroups (e.g., 1-8, 2-8, 3-8, 4-8, 5-8, 6-8, 7-8, 1, 2, 3, 4, 5, 6, 7, and 8 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. As used herein, $C_{1-3}$alkyl refers to methyl, ethyl, propyl, and isopropyl.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, «-butylene, ethenylene, propenylene, «-butenylene, propynylene, «-butynylene, and the like.

The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

As used herein, "haloalkyl" or "halo$C_{x-y}$alkyl" refers to an alkyl group in which one or more of the hydrogen atoms are replaced by halogen. Such groups include but are not limited to, chloromethyl, fluoromethyl, difluoromethyl, trifluoromethyl, 1,1-difluoroethyl, 2-fluoroethyl, 1-chloro-2-fluoromethyl and 2-fluoroisobutyl. A haloalkyl may be substituted or unsubstituted, and some embodiments relate to a medium size haloalkyl having 1 to 10 carbon atoms, such as $C_{1-6}$ haloalkyl. As used herein, halo$C_{1-3}$alkyl refers to a $C_{1-3}$alkyl group wherein one or more of the hydrogens are replaced by halo. Any suitable number of hydrogens can be replaced with halo. In some embodiments, only one hydrogen of the $C_{1-3}$alkyl group is replaced with halo. In some embodiments, all the hydrogens of the $C_{1-3}$alkyl group are replaced with halo (i.e., perhalogenated). In some embodiments, an intermediate number of hydrogens are replaced with halogen. Nonlimiting suitable halo$C_{1-3}$alkyl include, for example, $—CH_2X$, $—CHX_2$, $—CX_3$, $—CH_2—CH_2X$, $—CH_2—CHX_2$, $—CH_2—CX_3$, $—CX_2—CX_3$, $—CHX—CH_2X$, $—CHX—CX_3$ wherein X is halo (e.g., F). In some embodiments halo$C_{1-3}$alkyl is halomethyl. In some embodiments, halo$C_{1-3}$alkyl is trifluoromethyl.

As used herein, the term "spiro" refers to ring systems having one atom (usually a quaternary carbon) as the only common atom between two rings.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, carbocyclic aryl, heteroaryl, alkoxy, cycloalkyloxy, heterocycloalkyloxy, (carbocyclic aryl)oxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, (carbocyclic aryl)carbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "bridge" refers to a bond or an atom or an unbranched chain of atoms connecting two different parts of a molecule. The two atoms that are connected through the bridge (usually but not always, two tertiary carbon atoms) are denotated as "bridgeheads".

$R^1_m$ and $R^2_n$

Compounds of formula (I) comprise $R^1$ and $R^2$, wherein $R^1$ and $R^2$ are each independently halo, $C_{1-3}$alkyl, or halo$C_{1-3}$alkyl and m and n are each independently 0, 1, or 2.

In some embodiments, m is 0 such that $R^1$ is not present. In some embodiments, m is 1 such that one $R^1$ is present. In some embodiments, m is 2 such that two $R^1$ are present.

In some embodiments, n is 0 such that $R^2$ is not present. In some embodiments, n is 1 such that one $R^2$ is present. In some embodiments, n is 2 such that two $R^2$ are present.

In embodiments comprising two $R^1$ and/or two $R^2$ groups, the $R^1$ or $R^2$ groups can be arranged in any suitable manner on the respective rings (e.g., geminal, vicinal, or on non-adjacent carbon atoms).

In some embodiments, the ring to which $R^1$ is attached

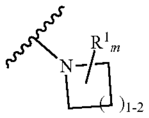

is 4-membered (i.e., substituted or unsubstituted azetidinyl)

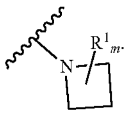

In some embodiments, the ring is 5-membered (i.e., substituted or unsubstituted pyrrolidinyl)

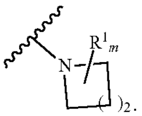

In some embodiments, m is 0 such that

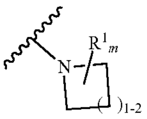

is

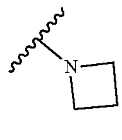

or

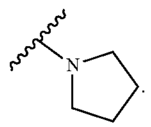

In some embodiments,

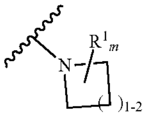

is

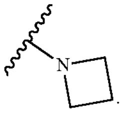 [SMILES: *N1CCC1]

In some embodiments, m is 1 and $R^1$ is —F, —Cl, —Br, —$CH_3$, or —$CF_3$.

In some embodiments, m is 2 and $R^1$ is F and $CF_3$. In some embodiments,

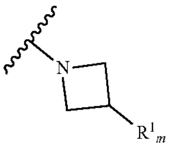

is

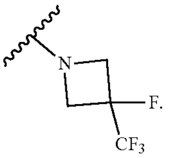

In some embodiments,

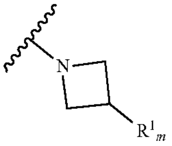

is

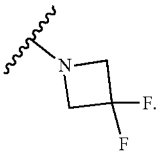 [SMILES: *N1CC(F)(F)C1]

In some embodiments,

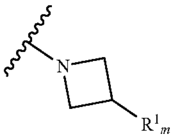

is

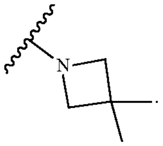 [SMILES: *N1CC(C)(C)C1]

In some embodiments, the ring to which $R^2$ is attached

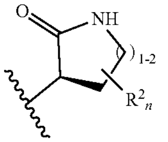

is 5-membered (i.e., substituted or unsubstituted γ-lactam

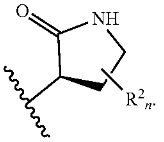

In some embodiments, the ring is 6-membered (i.e., substituted or unsubstituted δ-lactam)

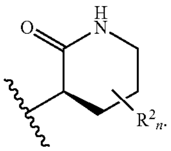

In some embodiments, n is 0 such that is

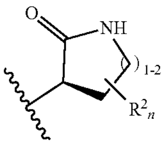

is

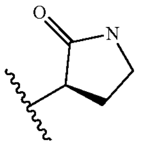 or 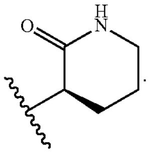

R$^3$ and R$^4$

Compounds of formula (I) comprise R$^3$ and R$^4$, wherein R$^3$ and R$^4$ are each independently H, $C_{1-3}$alkyl, halo$C_{1-3}$alkyl, or a 3 to 6-membered spiro ring optionally comprising 1 or 2 ring heteroatoms independently selected from N, O, and S, and the spiro ring is substituted with 0-2 $R^a$, or R$^3$ and R$^4$, taken together with the carbon atoms to which they are attached, form a $C_{3-6}$cycloalkyl substituted with 0-2 $R^a$.

In some embodiments, R$^3$ and R$^4$ are each independently H or $C_{1-3}$alkyl.

In some embodiments, R$^3$ and R$^4$ are a 3 to 6-membered spiro ring optionally comprising 1 or 2 ring heteroatoms independently selected from N, O, and S, and the spiro ring is substituted with 0-2 $R^a$. Suitable nonlimiting 3 to 6-membered spiro rings include, for example,

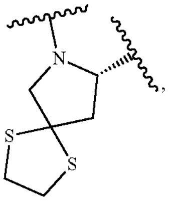 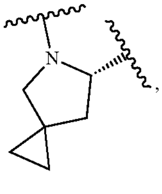 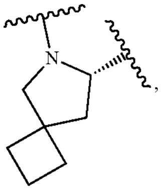 and

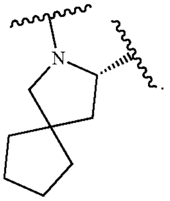

In some embodiments, R$^3$ and R$^4$ are taken together with the carbon atoms to which they are attached to form a $C_{3-6}$cycloalkyl substituted with 0-2 $R^a$. Suitable nonlimiting $C_{3-6}$cycloalkyl groups include, for example, cyclopropyl, cyclobutyl, cyclopentyl, and cyclohexyl. In some embodiments, the $C_{3-6}$-cycloalkyl is cyclopropyl or cyclopentyl.

In embodiments, wherein R$^3$ and/or R$^4$ is substituted by one or more $R^a$ substituents, each $R^a$ independently is halo, $C_{1-3}$alkyl, or halo$C_{1-3}$alkyl.

In some embodiments,

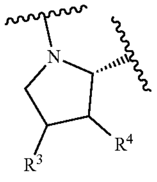

of compound of formula (I) is selected from:

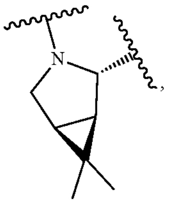 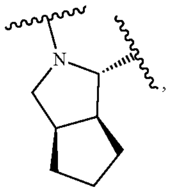 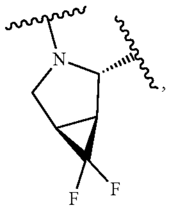

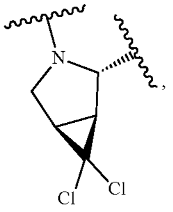 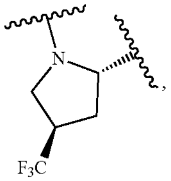 and 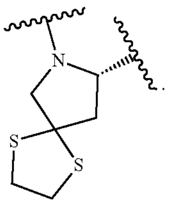

In some embodiments,

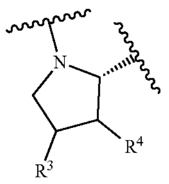

of compound of formula (I) is

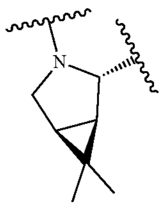 or 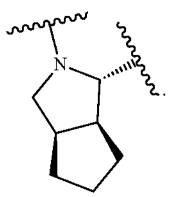

In some embodiments,

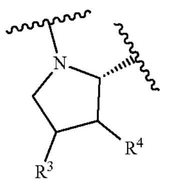

of compound of formula (I) is

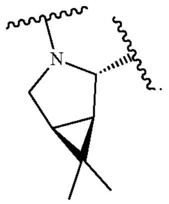 [SMILES: *[C@@H]1[C@@H]2[C@H](CN1*)C2(C)C]

$R^5$

Compounds of formula (I) comprise a $R^5$ moiety, wherein $R^5$ is $C_{1-3}$alkyl, isobutyl, bridged bicyclo$C_{5-8}$alkyl, alkylene-$C_{3-8}$cycloalkyl, alkylene-$C_{1-4}$alkoxy, alkylene-O—$C_{3-8}$cycloalkyl wherein the cycloalkyl is optionally substituted with $C_{1-3}$alkyl; or $R^5$ is $C_{3-8}$cycloalkyl optionally substituted with $C_{1-3}$alkyl, halo, halo$C_{1-4}$alkyl, or $C_{1-3}$alkoxy.

In some embodiments, $R^5$ is selected from

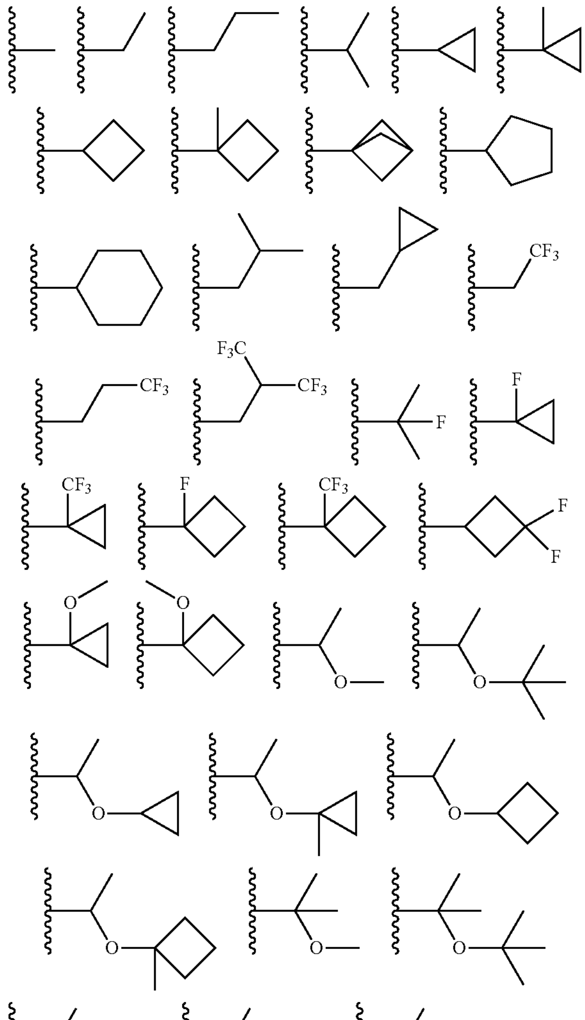

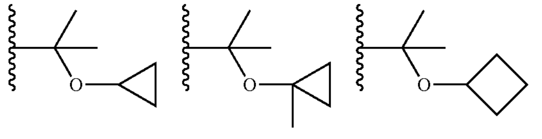

and

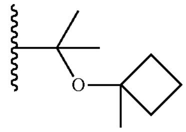

In some embodiments, $R^5$ is methyl, ethyl, 1-propyl, 2-propyl, cyclopropyl, cyclobutyl, cyclopentyl, cyclohexyl, isobutyl, or cyclopropyl-$CH_2$—.

In some embodiments, $R^5$ is 2-propyl. In some embodiments, $R^5$ is cyclohexyl.

$R^6$

Compounds of formula (I) comprise a $R^6$ moiety, wherein $R^6$ is $C_{1-3}$alkyl, halo$C_{1-6}$alkyl, $C_{1-4}$alkoxy, $C_{3-6}$cycloalkoxy, or -haloalkylene-$C_{3-6}$-cycloalkyl.

In some embodiments, $R^6$ is

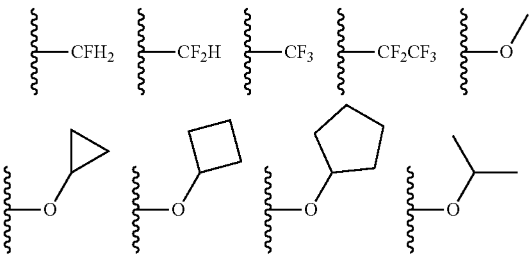

or

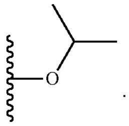

.

In some embodiments, $R^6$ is trifluoromethyl.

Compounds of Formulae (IA)-(IF)

In some embodiments, the disclosure provides compounds of formula (IA):

(IA)

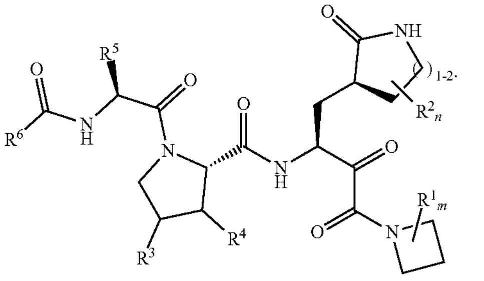

In some embodiments, the disclosure provides compounds of formula (IB):

(IB)

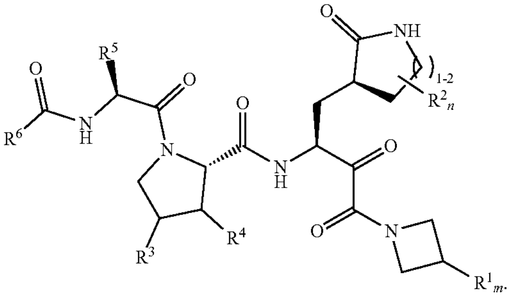

In some embodiments, $R^1_m$ of compounds of formula (IB) is —F, —Cl, —Br, —$CH_3$, or —$CF_3$. In some embodiments, the compound of formula (IA) or (IB) is (IB)

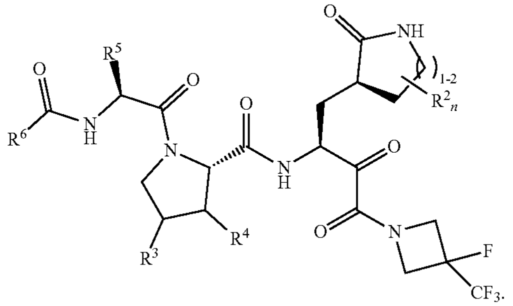

In some embodiments, the disclosure provides compounds of formula (IC) or (ID):

(IC)

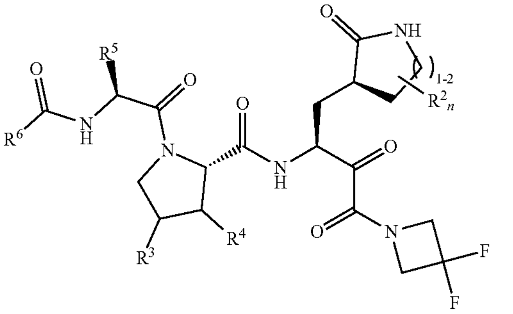

(ID)

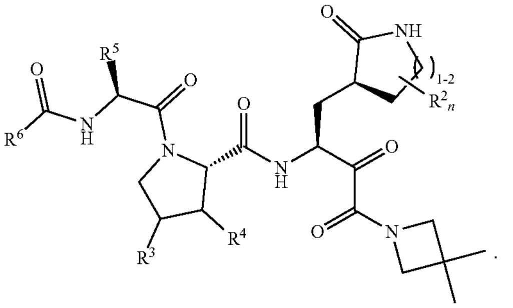

In some embodiments, the disclosure provides compounds of formula (IE):

(IE)

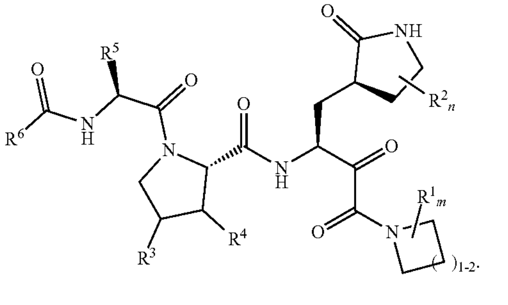

In some embodiments, the disclosure provides compounds of formula (IF):

(IF)

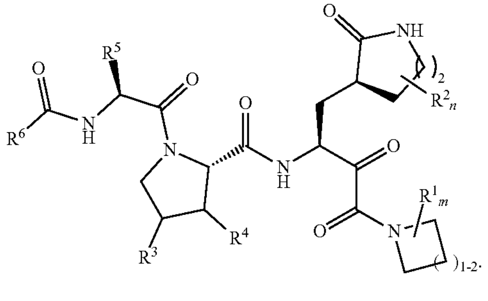

Compounds of Formula (I-1), (I-2), (I-3), and (I-4)

In some embodiments, the disclosure provides a compound characterized by a structure selected from (I-1)

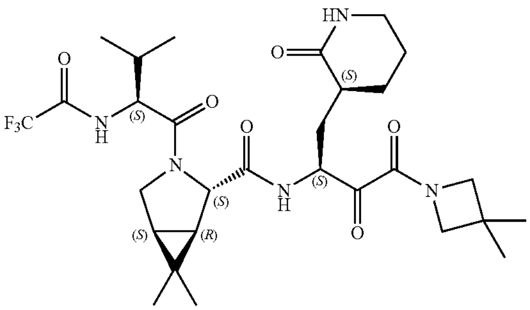

, (I-2)

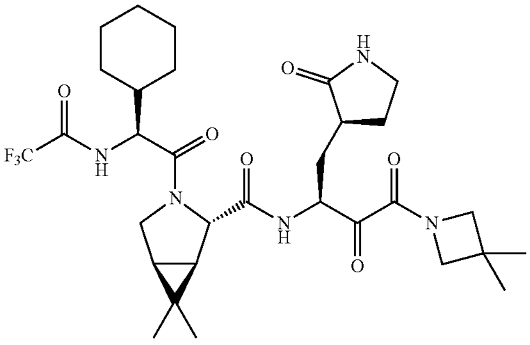

, (I-3)

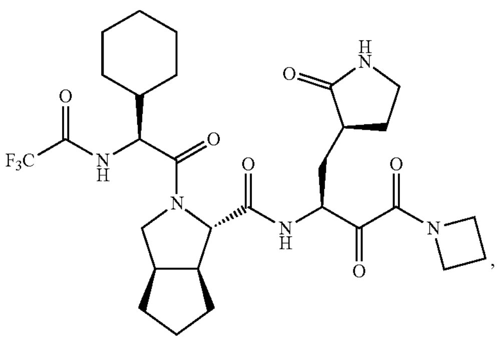

, and

-continued (I-4)

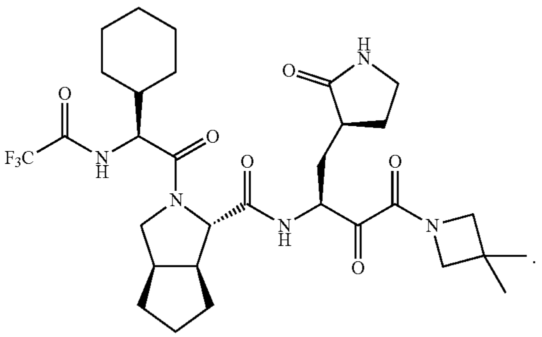

In some embodiments, the disclosure provides a compound characterized by the structure for formula (I-1):

(I-1)

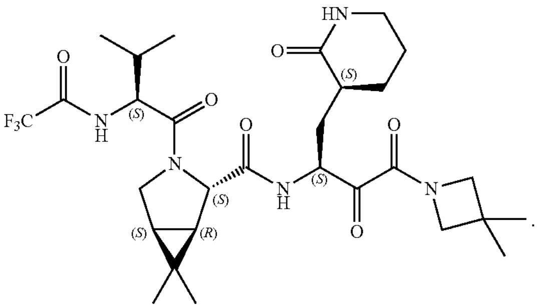

Compound of Formula (II)

In some embodiments, the disclosure provides a compound of formula (II):

(II)

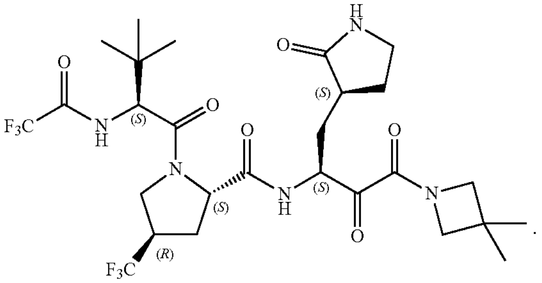

Pharmaceutical Compositions

In some embodiments, the disclosure provides pharmaceutical compositions comprising the disclosed compounds (e.g., compounds of formula (I), (II), (IA), (IB), (IC), (ID), (IE), (IF), (I-1), (I-2), (I-3), and/or (I-4) and a pharmaceutically acceptable carrier.

In some embodiments, the disclosed pharmaceutical compositions comprise a pharmaceutically acceptable salt, solvate, or hydrate of the disclosed compounds and a pharmaceutically acceptable carrier.

In some embodiments, the pharmaceutical composition is formulated for oral, parenteral, inhalational, intranasal, subcutaneous, intramuscular, or intravenous administration. In some embodiments, the pharmaceutical composition is formulated for oral administration.

In some embodiments, the pharmaceutical composition further comprises an additional pharmaceutical used for treating a SARS-CoV-2 infection.

In certain aspects, a composition of the present disclosure includes the compound present in a liquid medium. The liquid medium may be an aqueous liquid medium, such as water, a buffered solution, or the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a nuclease inhibitor, a protease inhibitor, glycerol, a chelating agent, and the like may be present in such compositions.

In some embodiments, a pharmaceutical composition of the present disclosure includes an effective amount of one or more of any of the compounds of the present disclosure, and a pharmaceutically acceptable carrier.

Any of the pharmaceutical compositions of the present disclosure may comprise a "cocktail" of two or more different antiviral agents (e.g., anti-coronavirus agents, such as two or more different anti-SARS-CoV-2 agents), where at least one of the agents is a compound of the present disclosure. In some embodiments, metformin is the antiviral agent. In certain embodiments, the pharmaceutical composition further comprises a coronavirus polymerase inhibitor, e.g., a SARS-CoV-2 polymerase inhibitor. According to some embodiments, the coronavirus polymerase inhibitor is selected from Remdesivir, Obeldesivir, GS-441524, GS-621763, favipiravir, molnupiravir, 4'-fluorouridine, VV116, and any combination thereof.

The compounds of the present disclosure can be incorporated into a variety of formulations for therapeutic administration. More particularly, a compound of the present disclosure can be formulated into pharmaceutical compositions by combination with appropriate, pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the compounds for administration to an individual (e.g., suitable for human administration) are generally sterile and may further be free of detectable pyrogens or other contaminants contraindicated for administration to a patient according to a selected route of administration, including but not limited to, parenteral, inhalational, intranasal, subcutaneous, intramuscular, and/or intravenous administration.

In pharmaceutical dosage forms, the compound can be administered in the form of their pharmaceutically acceptable salts, or they may also be used alone or in appropriate association, as well as in combination, with other pharmaceutically active compounds. The following methods and carriers/excipients are merely examples and are in no way limiting.

For oral preparations, the compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A compound of the present disclosure can be formulated for parenteral (e.g., intravenous, intra-arterial, intraosseous, intramuscular, intracerebral, intracerebroventricular, intrathecal, subcutaneous, etc.) administration. In certain aspects, the compound is formulated for injection by dissolving, suspending or emulsifying the compound in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions that include a compound of the present disclosure may be prepared by mixing the compound having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of a compound of the present disclosure may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included to modulate the tonicity of the formulation. Example tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 mM.

A surfactant may also be added to the formulation to reduce aggregation and/or minimize the formation of particulates in the formulation and/or reduce adsorption. Example surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Example concentrations of surfactant may range from about 0.001% to about 1% w/v.

A lyoprotectant may also be added in order to protect the compound against destabilizing conditions during a lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, the pharmaceutical composition includes a compound of the present disclosure, and one or more of the above-identified components (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

A pharmacokinetic enhancing compound may be included in a composition to reduce the metabolism of the CoV $M^{pro}$ inhibitor and thereby increase its exposure in mammals. Pharmacokinetic enhancing compounds may beneficially inhibit at least one isoform of the cytochrome P450 (CYP450) enzymes. The isoforms of CYP450 that may be beneficially inhibited include, but are not limited to CYP1A2, CYP2D6, CYP2C9, CYP2C19 and CYP3A4. A non-limiting example includes the inhibition of CYP3A by ritonavir to reduce the clearance of the $M^{pro}$ inhibitor compound.

A pharmacodynamic and/or pharmacokinetic enhancing compound may be included in a composition to reduce $M^{pro}$ inhibitor efflux from CoV infected cells expressing efflux pumps such as but not limited to P-glycoprotein. Examples of P-glycoprotein inhibitors are verapamil, vinblastine, ketoconazole, 5 nelfinavir, ritonavir or cyclosporine. Furthermore, the $M^{pro}$ inhibitor compound can in some embodiments itself act as a P-glycoprotein inhibitor. Inhibition of the P-glycoprotein efflux will result in larger intracellular concentrations of the CoV $M^{pro}$ inhibitor to improve the antiviral effect (i.e., lower the $EC_{50}$) thereby improving the pharmacokinetics. Furthermore, inhibition of efflux pumps may also improve the pharmacokinetics, for example, the oral bioavailability.

In the case of coronavirus $M^{pro}$ inhibitor compounds, prodrugs, salts, or solvates that are solids, it is understood that a composition of the compound, prodrugs, salts, and solvates may exist in different polymorph or crystal forms, all of which are intended to be within the scope of the present invention and specified formulas.

Methods of Use

In some embodiments, the present disclosure provides methods comprising administering a compound of the present disclosure to an individual in need thereof, e.g., an individual having or suspected of having a viral infection, such as a coronavirus infection (e.g., a SARS-CoV-2 infection). In certain embodiments, provided are methods of treating or preventing a viral infection in an individual, the method comprising administering to the individual a pharmaceutical composition comprising a therapeutically effective amount of any of the compounds of the present disclosure. In certain embodiments, the method is for treating or preventing a SARS-CoV-2 infection in the individual.

In one aspect, the scope of the invention encompasses the administration of a compound of the present disclosure for the prevention or treatment of a viral infection. In one aspect the scope of the invention encompasses the administration of a compound of the present disclosure for the inhibition of a viral protease, for example any of: a cysteine protease, a C3 protease, a C3-like protease, a papain protease, a papain-like protease, and/or a protease selected from the group consisting of 3-chymotrypsin-like protease (3CLpro), non-structural protein 5 protease (nsp5), main protease (Mpro), papain-like protease protein (PLPpro), PLP1, and PLP2. In various embodiments, a compound of the present disclosure is used in a method of preventing or treating an infection caused by a virus and/or inhibiting a protease of a virus, wherein the virus is any of: an RNA virus; a positive-strand RNA virus; a coronavirus, including for example SARS-CoV-2, SARS-CoV, MERS, HKU1 beta coronavirus, OC43 beta corona virus, NL63 alpha coronavirus, and 229E alpha coronavirus; a norovirus, including for example genogroup II genotype 4 norovirus (GII.4), genogroup II genotype 2 norovirus (GII.2) and genogroup II genotype 17 norovirus (GII. 17); a virus selected from any of: influenza, MD145, feline infectious peritonitis virus, EV-68 virus, EV-71 virus, poliovirus, hepatitis virus including hepatitis A, B, or C virus, foot-and-mouth disease virus (FMDV), calicivimses, Picornaviruses enteroviruses, enterovirus 71, poliovirus, coxsackievirus, foot-and-mouth disease virus (FMDV), hepatitis A virus (HAV), porcine teschovirus, rhinovirus, and porcine teschovirus.

The pharmaceutical composition may be administered to any of a variety of individuals. In certain aspects, the individual is a "mammal" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual is a human. In certain embodiments, the individual is an animal model (e.g., a mouse model, a primate model, or the like) of a SARS-CoV-2 infection, e.g., an animal model of COVID-19.

The compound is administered in a therapeutically effective amount. By "therapeutically effective amount" is meant a dosage sufficient to produce a desired result, e.g., an amount sufficient to effect beneficial or desired therapeutic (including preventative) results, such as a reduction in a symptom of a SARS-CoV-2 infection (e.g., a symptom of COVID-19), as compared to a control. In some embodiments, the therapeutically effective amount is sufficient to slow the progression of, or reduce, one or more symptoms of a SARS-CoV-2 infection (e.g., one or more COVID-19 symptoms) selected from viral load, hypoxia (e.g., oxygen saturation levels below 95%, e.g., as measured by pulse oximetry), pneumonia, acute respiratory distress syndrome, thrombosis in the pulmonary microcirculation, and/or the like. According to some embodiments, the therapeutically effective amount slows the progression of, or reduces, one or more of such symptoms by 10% or more, 20% or more, 30% or more, 40% or more, 50% or more, 60% or more, 70% or more, 80% or more, 90% or more, or 100% or more, as compared to the one or more symptoms in the absence of the administration of the compound. An effective amount can be administered in one or more administrations.

When the methods include administering a combination of a compound of the present disclosure and a second agent (e.g., a second agent approved for treatment of a SARS-CoV-2 infection, e.g., COVID-19, non-limiting examples of which are the antiviral agent metformin or a SARS-CoV-2 polymerase inhibitor, e.g., remdesivir, Obeldesivir, GS-441524, GS-621763, favipiravir, molnupiravir, 4'-fluorouridine, VV116, or any combination thereof), the compound and the second agent may be administered concurrently (e.g., in the same or separate formulations), sequentially, or both. For example, according to certain embodiments, the second agent is administered to the individual prior to administration of the compound, concurrently with administration of the compound, or both. In some embodiments, the compound is administered to the individual prior to administration of the second agent, concurrently with administration of the second agent, or both.

In some embodiments, the one or more agents are administered according to a dosing regimen approved for individual use. In some embodiments, the administration of the compound permits the second agent to be administered according to a dosing regimen that involves one or more lower and/or less frequent doses, and/or a reduced number of cycles as compared with that utilized when the second agent is administered without administration of the compound. In some embodiments, the administration of the second agent permits the compound to be administered according to a dosing regimen that involves one or more lower and/or less frequent doses, and/or a reduced number of cycles as compared with that utilized when the compound is administered without administration of the second agent.

Desired relative dosing regimens for agents administered in combination may be assessed or determined empirically, for example using ex vivo, in vivo and/or in vitro models; in some embodiments, such assessment or empirical determination is made in vivo, in a patient population (e.g., so that a correlation is established), or alternatively in a particular subject of interest.

A compound of the present disclosure, and if also administered, a second agent, may be administered via a route of administration independently selected from oral, parenteral (e.g., by intravenous, intra-arterial, subcutaneous, intramuscular, or epidural injection), inhalational, or intranasal administration.

As described above, aspects of the present disclosure include methods for treating an individual having or suspected of having a coronavirus (e.g., SARS-CoV-2) infection, e.g., COVID-19. By treatment is meant at least an amelioration of one or more symptoms associated with the coronavirus (e.g., SARS-CoV-2) infection (e.g., COVID-19) of the individual, where amelioration is used in a broad sense to refer to at least a reduction in the magnitude of a parameter, e.g., symptom, associated with the coronavirus infection. Non-limiting examples of such symptoms include one or more of viral load, hypoxia (e.g., oxygen saturation levels below 95%, e.g., as measured by pulse oximetry), pneumonia, acute respiratory distress syndrome, thrombosis in the pulmonary microcirculation, and/or the like. As such, treatment also includes situations where the coronavirus infection, or at least one or more symptoms associated therewith, are completely inhibited, e.g., prevented from happening, or stopped, e.g., terminated, such that the individual no longer suffers from the coronavirus infection, or at least the symptoms that characterize the coronavirus infection.

When the methods of treatment are for treating COVID-19, it is to be understood that COVID-19 is the disease caused in patients by infection with the SARS-CoV-2 virus. The SARS-CoV-2 virus is to be understood to encompass the initially discovered strain of the virus as well as variants which have emerged, such as but not limited to, Alpha, Beta, Gamma, Delta and Omicron, sublineages thereof, and future emerging variants including variants that resist treatment with current or future antivirals.

The $K_i$ refers to the inhibition equilibrium constant ($K_i$) of the compounds for inhibition of proteolytic activity of purified $M^{pro}$-coil. $EC_{50}$ refers to the half maximal effective concentration of antiviral activity of the compounds in cell culture. The term "pharmaceutically acceptable" means the substance or composition must be compatible, chemically and/or toxicologically, with the other ingredients comprising a formulation, and/or the mammal being treated therewith.

It is to be understood that descriptions related to the main protease ($M^{pro}$) of SARS-CoV-2 and interactions between inhibitors and SARS-CoV-2 $M^{pro}$ serve as non-limiting examples of the invention. Specifically, the invention also pertains to other cysteine proteases, particularly, 3C-like proteases of other viruses such as but not limited to other coronaviruses, noroviruses, and enteroviruses.

EMBODIMENTS

1. A compound having a structure of formula (I) or formula (II):

(I)

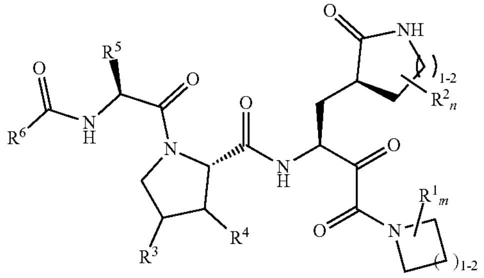

or

-continued (II)

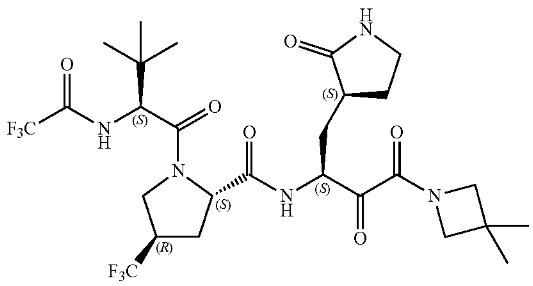

, or a pharmaceutically acceptable salt, solvate, or hydrate thereof, wherein $R^1$ and $R^2$ are each independently halo, $C_{1-3}$alkyl, or halo$C_{1-3}$alkyl;

m and n are each independently 0, 1, or 2;

$R^3$ and $R^4$ are each independently H, $C_{1-3}$alkyl, halo$C_{1-3}$ alkyl, or a 3 to 6-membered spiro ring optionally comprising 1 or 2 ring heteroatoms independently selected from N, O, and S, and the spiro ring is substituted with 0-2 $R^a$, or $R^3$ and $R^4$, taken together with the carbon atoms to which they are attached, form a $C_{3-6}$-cycloalkyl substituted with 0-2 $R^a$;

each $R^a$ is independently halo, $C_{1-3}$alkyl, or halo$C_{1-3}$ alkyl;

$R^5$ is $C_{1-3}$alkyl, isobutyl, bridged bicyclo$C_{5-8}$-alkyl, alkylene-$C_{3-8}$cycloalkyl, alkylene-$C_{1-4}$alkoxy, alkylene-O—$C_{3-8}$cycloalkyl wherein the cycloalkyl is optionally substituted with $C_{1-3}$alkyl; or $C_{3-8}$-cycloalkyl optionally substituted with $C_{1-3}$alkyl, halo, halo$C_{1-4}$ alkyl, or $C_{1-3}$alkoxy; and $R^6$ is $C_{1-3}$alkyl, halo$C_{1-6}$alkyl, $C_{1-4}$alkoxy, $C_{3-6}$cycloalkoxy, or -haloalkylene-$C_{3-6}$cycloalkyl.

2. The compound according to embodiment 1, wherein

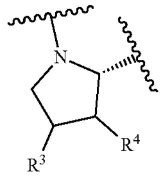

is selected from:

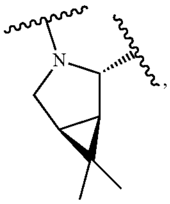

,

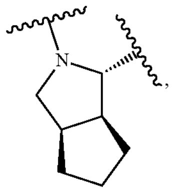

,

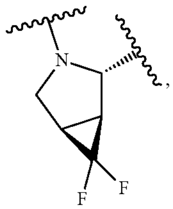

,

-continued

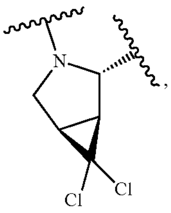,

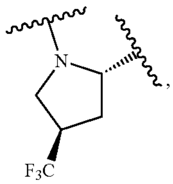, and

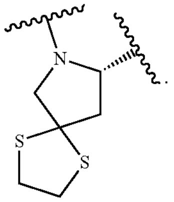

3. The compound according to embodiment 2, wherein

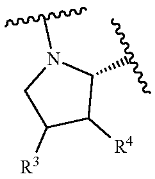

is:

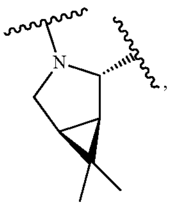, or

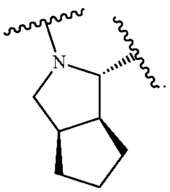

4. The compound according to embodiment 3, wherein

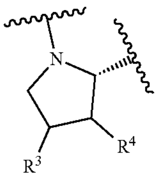

is:

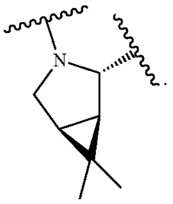 [SMILES: *[C@@H]1[C@@H]2[C@H](CN1*)C2(C)C]

5. The compound according to any one of embodiments 1-4, characterized by formula (IA):

(IA)

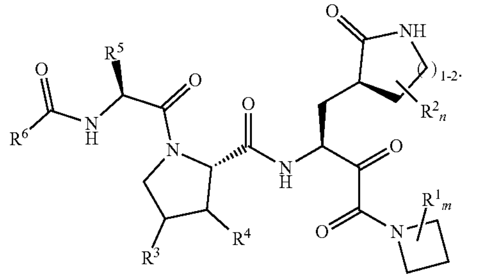

6. The compound according to embodiment 5, characterized by formula (IB):

(IB)

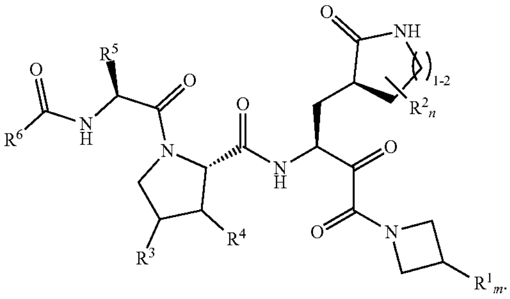

7. The compound according to embodiment 6, wherein m is 1 and $R^1$ is —F, —Cl, —Br, —$CH_3$, or —$CF_3$.

8. The compound according to embodiment 6, wherein m is 2 and

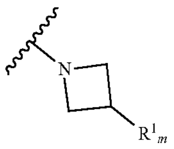

is

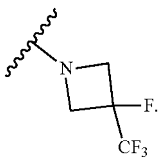 [SMILES: *N1CC(F)(C(F)(F)F)C1]

9. The compound according to embodiment 5 or 6, characterized by formula (IC) or (ID)

(IC)

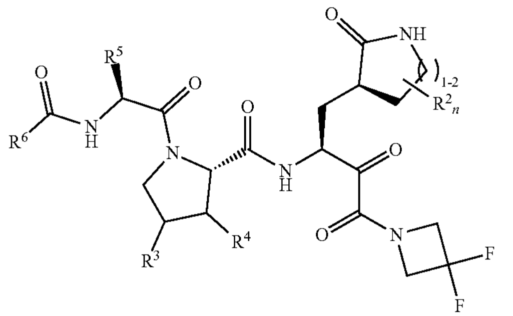

(ID)

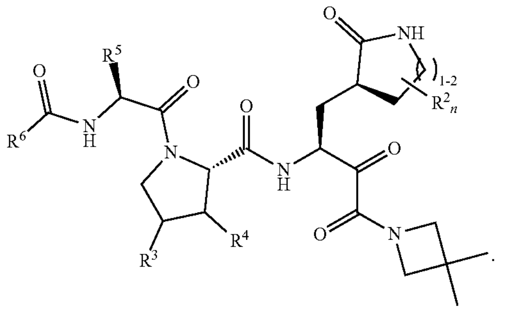

10. The compound according to any one of embodiments 1-9, characterized by formula (IE):

(IE)

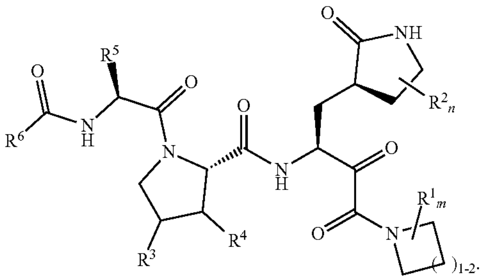

11. The compound according to any one of embodiments 1-9, characterized by formula (IF):

(IF)

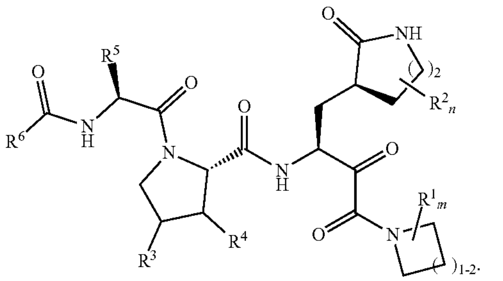

12. The compound according to any one of embodiments 1-11, wherein $R^5$ is

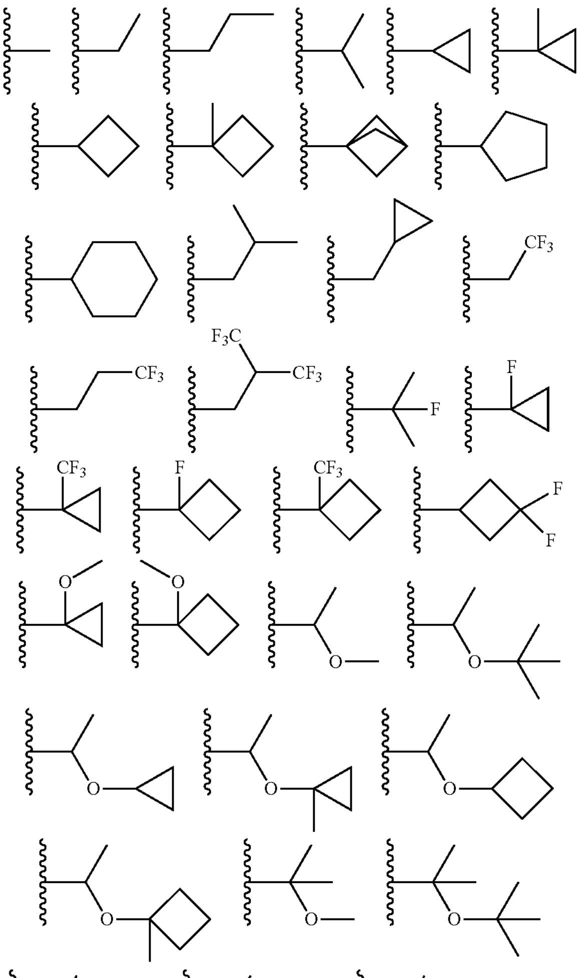

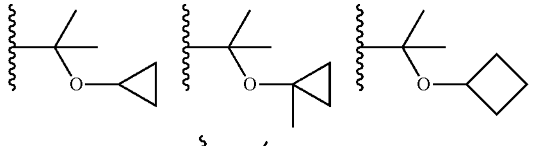

or

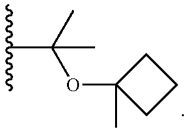

13. The compound according to any one of embodiments 1-12, wherein $R^5$ is methyl, ethyl, 1-propyl, 2-propyl, cyclopropyl, cyclobutyl, cyclopentyl, cyclohexyl, isobutyl, or cyclopropyl-$CH_2$—.

14. The compound according to embodiment 13, wherein $R^5$ is 2-propyl.

15. The compound according to embodiment 13, wherein $R^5$ is cyclohexyl.

16. The compound according to any one of embodiments 1-15, wherein $R^6$ is

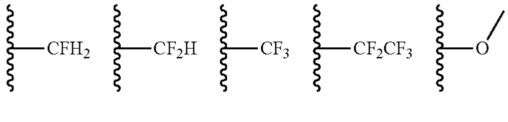

-continued

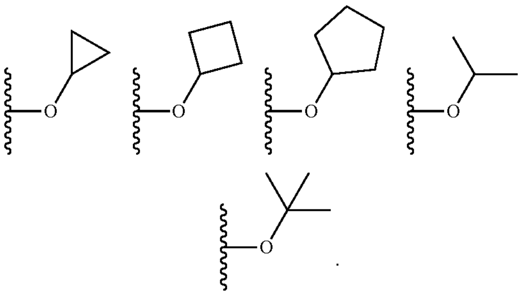

or

17. The compound according to any one of embodiments 1-16, wherein $R^6$ is trifluoromethyl.

18. The compound according to any one of embodiments 1-16, wherein $R^6$ is methoxy.

19. The compound according to embodiment 1 characterized by a structure selected from:

(I-1)

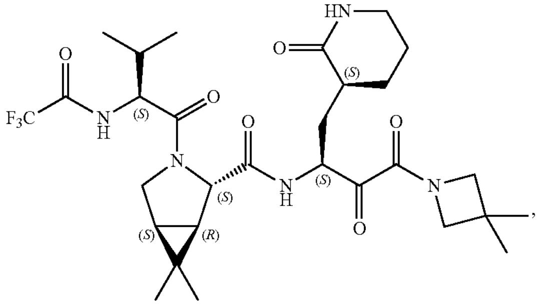

(I-2)

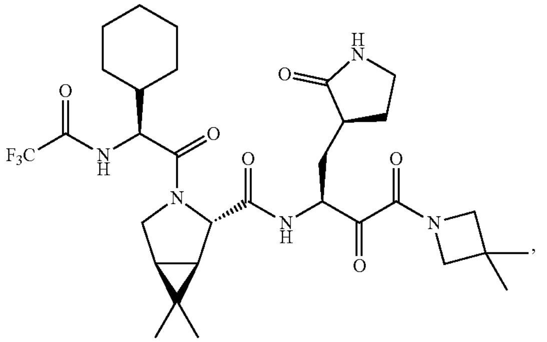

(I-3)

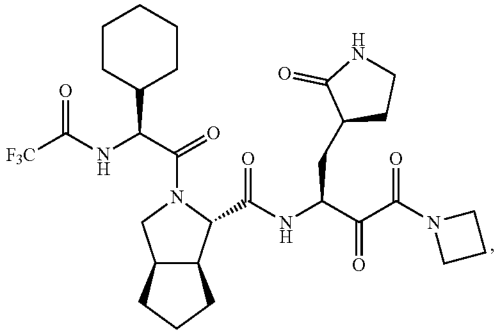

-continued (I-4)

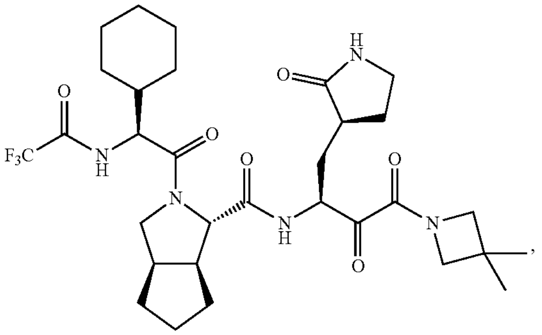

and (II)

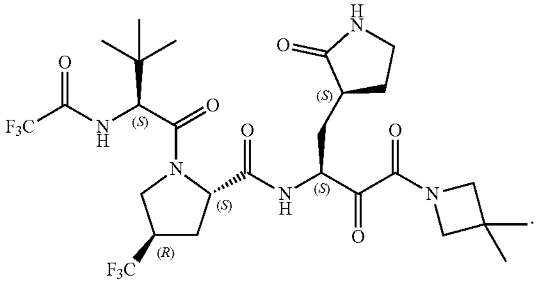

20. The compound of embodiment 19 having the structure of:

(I-1)

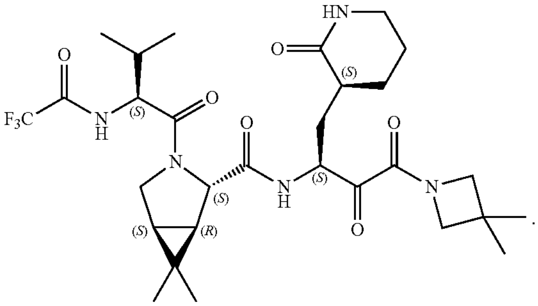

21. A pharmaceutical composition comprising the compound of any one of embodiments 1-20 and a pharmaceutically acceptable carrier.

22. The pharmaceutical composition of embodiment 21, wherein the pharmaceutical composition is formulated for oral, parenteral, inhalational, intranasal, subcutaneous, intramuscular, or intravenous administration.

23. The pharmaceutical composition of embodiment 22, wherein the pharmaceutical composition is formulated for oral administration.

24. The pharmaceutical composition of any one of embodiments 21-23, further comprising a second therapeutic agent used for treating a SARS-CoV-2 infection.

25. A method of treating or preventing a viral infection in an individual, comprising administering to an individual the therapeutically effective amount of the pharmaceutical composition of any one of embodiments 21-24.

26. The method according to embodiment 25, wherein the viral infection is a coronavirus infection, norovirus infection, or enterovirus infection.

27. The method according to embodiment 26, wherein the coronavirus infection is a SARS-CoV-2 infection.

EXAMPLES

The following examples further illustrate the disclosed methods of treatment, but of course, should not be construed as in any way limiting its scope.

Example 1A—Illustrative Synthesis of a Compound of Formula (I)

Intermediate compounds useful in processes for preparing a compound of formula (I-1) were prepared using the following processes.

Synthesis of Intermediate 18

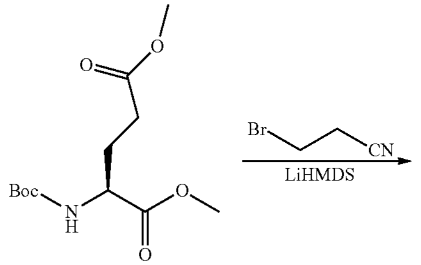

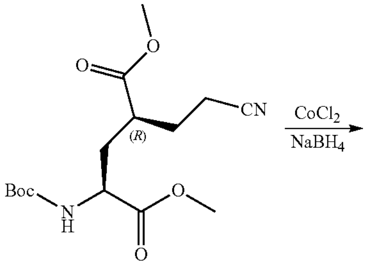

15

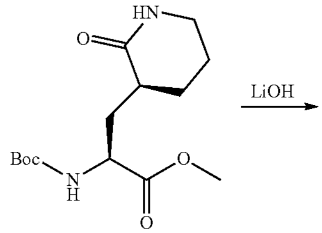

16

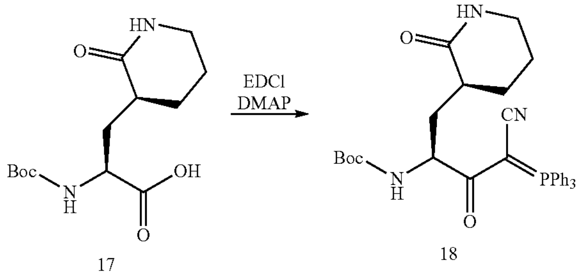

17 18 dimethyl (2S,4S)-2-((tert-butoxycarbonyl)amino)-4-(2-cyanoethyl)pentanedioate (15): To a solution of dimethyl (tert-butoxycarbonyl)-L-glutamate (54.0 g, 196 mmol) in anhydrous THF (1.0 L) was added the solution of LiHMDS/THF (432 mL, 1 mol/L, 432 mmol, 2.2 equiv) drop-wise under $N_2$ atmosphere at −78° C. After a further 2 h of stirring at −78° C., 3-bromopropanenitrile (39.4 g, 294 mmol, 1.5 equiv) was added dropwise to the mixture solution over a period of 1 h while maintaining the temperature under −78° C. The reaction mixture was stirred at −78° C. for additional 1-2 h under the $N_2$ atmosphere and quenched with pre-cooled MeOH (100 mL) and a pre-cooled AcOH in THE solution (20 mL AcOH/160 mL THF) in order. After a further 30 min of stirring at −78° C., the cooling bath was removed and replaced with water bath. The reaction mixture was allowed to warm up to 0±5° C. and then the solvents were evaporated to give the yellow solid. The obtained residue was dissolved in EtOAc (600 mL), washed with brine (300 mL×2). The organic phase was dried over $Na_2SO_4$, concentrated and the residue was purified by silica gel column chromatography eluted with EtOAc/PE 1:4 to give 15 as a light-yellow oil (20.0 g, 31%). MS (ESI): m/z 329 $[M+H]^+$.

methyl(S)-2-((tert-butoxycarbonyl)amino)-3-((S)-2-oxopiperidin-3-yl)propanoate (16): To a solution of 15 (20.0 g, 61.0 mmol) in MeOH (400 mL) was added $CoCl_2$ (4.76 g, 36.6 mmol, 0.6 equiv) at 0° C. $NaBH_4$ (13.9 g, 366 mmol, 6 equiv) was added portion-wise at 0° C. Then the reaction mixture was stirred at RT for 12 h. Saturated ammonium chloride solution (200 mL) was added to quench the reaction and the mixture was filtered. MeOH in the filtrate was evaporated and the residual mixture was extracted with DCM (250 mL×3). The combined organic layer was washed with brine (200 mL×3). The organic phase was dried over $Na_2SO_4$, concentrated and the residue was purified by silica gel column chromatography eluted with EtOAc/PE 1:2 to give 16 as a light yellow oil (5.5 g, 30%). MS(ESI): m/z 323 $[M+Na]^+$. $^1H$ NMR (400 MHZ, $CDCl_3$) δ: 5.90 (brs, 1H), 5.60 (brs, 1H), 4.36-4.31 (m, 1H), 3.74 (s, 3H), 3.34-3.31 (m, 2H), 2.40-2.26 (m, 2H), 2.18-2.14 (m, 1H), 1.95-1.81 (m, 2H), 1.62-1.53 (m, 2H), 1.45 (s, 9H).

(S)-2-((tert-butoxycarbonyl)amino)-3-((S)-2-oxopiperidin-3-yl)propanoic acid (17): To a solution of 16 (5.5 g, 18.3 mmol, 1.0 equiv) in THF (100 mL) was added 2 N aq. LiOH (18.3 mL, 36.6 mmol, 2.0 equiv). The mixture was stirred at RT for 2 h. Upon completion, the mixture was acidified with 2 N aq. hydrochloride until pH 3, extracted with EtOAc (100 mL×2), dried and evaporated under reduced pressure to get 17 as an off-white solid (4.6 g, 88%). MS (ESI): m/z 287 $[M+H]^+$.

tert-butyl ((S)-4-cyano-3-oxo-1-((S)-2-oxopiperidin-3-yl)-4-(triphenyl-15-phosphaneylidene) butan-2-yl)carbamate (18): To a solution of 17 (4.6 g, 16.1 mmol, 1.0 equiv) in DCM (100 mL) was added (cyanomethylene)triphenylphosphorane (5.33 g, 17.7 mmol, 1.1 equiv), DMAP (220 mg, 1.8 mmol, 0.1 equiv) and EDCl HCl (3.39 g, 17.7 mmol, 1.1 equiv) under $N_2$ at RT. Then the mixture was stirred at this temperature for 5 h. Upon completion, the mixture was quenched with sat. $NaHCO_3$ (200 mL), extracted with DCM (150 mL×2), dried and evaporated in vacuo to get the residue which was purified by silica gel column chromatography eluted with DCM/MeOH 95:5 to yield 18 as an off-white solid (4.3 g, 47%). MS (ESI): m/z 570 $[M+H]^+$.

Synthesis of Intermediates w2-a4

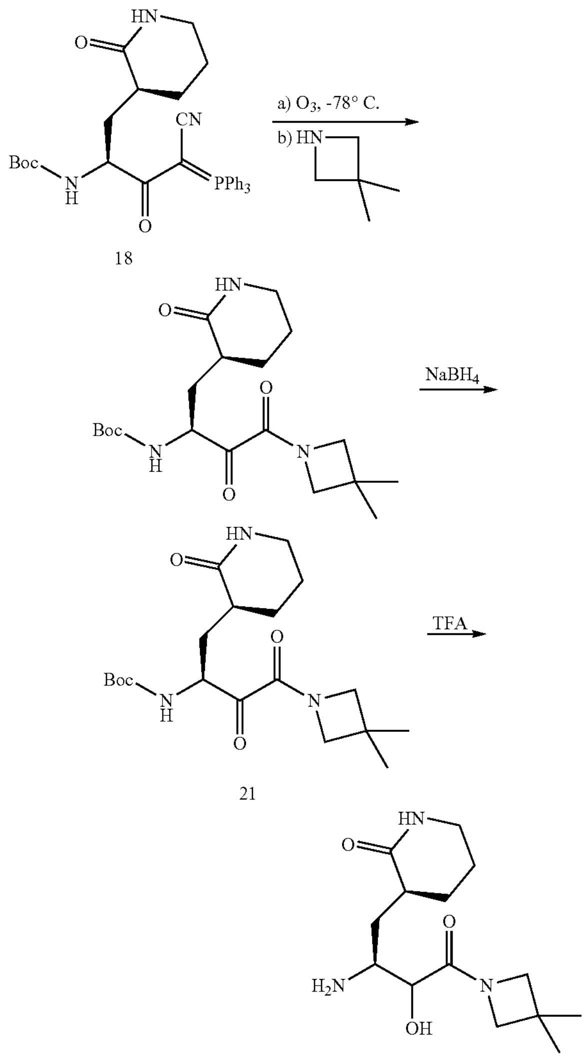

18

21 w2-a4 tert-butyl (2S)-4-(3,3-dimethylazetidin-1-yl)-3-hydroxy-4-oxo-1-((S)-2-oxopiperidin-3-yl)butan-2-ylcarbamate (21): To a solution of 18 (1.0 g, 1.76 mmol, 1.0 equiv) in DCM (40 mL) was bubbled $O_3$ at −78° C. until a blue color formed, then $N_2$ was further bubbled into the mixture for about 15 mins to exchange the $O_3$, followed by the addition of 3,3-dimethylazetidine (449 mg, 5.28 mmol, 3.0 equiv). After stirring for 0.5 h at −78° C., $NaBH_4$ (201 mg, 5.28 mmol, 3.0 equiv) and MeOH (5 mL) were added into the mixture, then it was stirred and allowed to warm to RT. Upon completion, the mixture was evaporated in vacuo to give the residue which was purified by reverse phase column chromatography eluted with water (0.05% aq. TFA)/MeCN 75:25 to obtain 21 (200 mg, 30%). MS(ESI): m/z 384 $[M+H]^+$.

(3S)-3-((2S)-2-amino-4-(3,3-dimethylazetidin-1-yl)-3-hydroxy-4-oxobutyl)piperidin-2-one trifluoroacetic acid salt (w2-a4): To a solution of 21 (200 mg, 0.52 mmol, 1.0 equiv) in DCM (6 mL) was added TFA (2 mL) at 0° C. Then the mixture was stirred at this temperature for 2 h. Upon completion, the mixture was evaporated in vacuo below 10° C. to obtain w2-a4 as a yellow oil (220 mg, 100%). MS (ESI): m/z 284 $[M+H]^+$.

The fragment of formula:

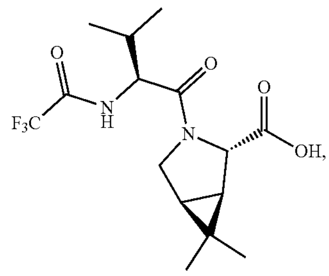 [SMILES: CC(C)[C@H](NC(=O)C(F)(F)F)C(=O)N1C[C@H]2[C@@H]([C@H]1C(=O)O)C2(C)C]

which contains the P2-P4 groups of peptidomimetic $M^{pro}$ inhibitors, was prepared using standard methods and reacted with intermediate compound w2-a4 under standard amide-bond forming conditions to provide compound of formula (I-1).

The product compound of formula (I-1) was confirmed by ESI LC/MS of the protonated compound and by $^1H$ NMR spectroscopy. The expected mass of Compound (I-1) was 613.3 and the mass found $[M+H]^+$ was 614.3. $^1H$ NMR (400 MHZ, DMSO-d6) δ: 9.93-7.19 (m, 3H), 5.02-4.74 (m, 1H), 4.29-3.90 (m, 4H), 3.88-3.39 (m, 4H), 3.14-3.02 (m, 2H), 2.38-1.90 (m, 4H), 1.77-1.17 (m, 12H), 1.06-0.80 (m, 12H). (400 MHZ, $CDCl_3$) δ: 9.15-7.95 (m, 1H), 7.16-6.92 (m, 1H), 5.96-5.72 (m, 1H), 5.14-4.79 (m, 1H), 4.60-4.47 (m, 1H), 4.29-4.29 (m, 1H), 4.24-3.56 (m, 6H), 3.38-3.24 (m, 2H), 2.76-1.74 (m, 7H), 1.62-1.44 (m, 3H), 1.32-1.24 (m, 6H), 1.09-0.80 (m, 12H).

Example 1B—Illustrative Synthesis of a Compound of Formula (I-2)

(I-2)

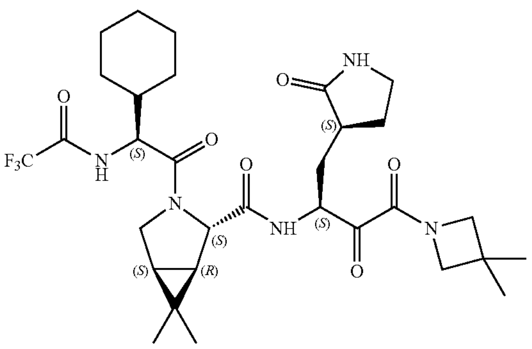

Scheme S1: Synthetic Route for Compound (1-2).

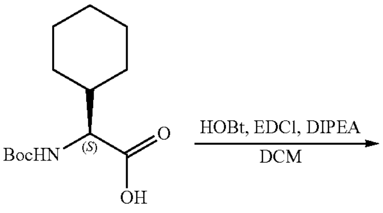

1B-1

-continued
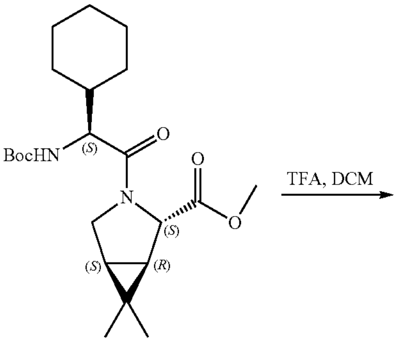
1B-2
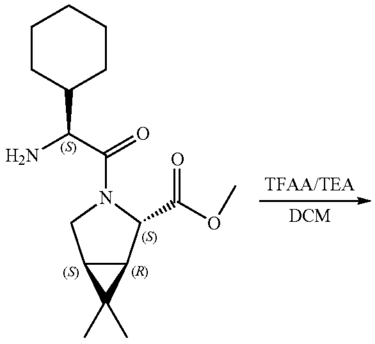
1B-3
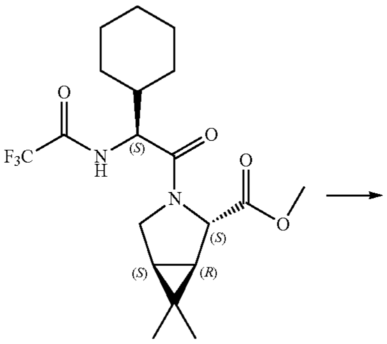
1B-4
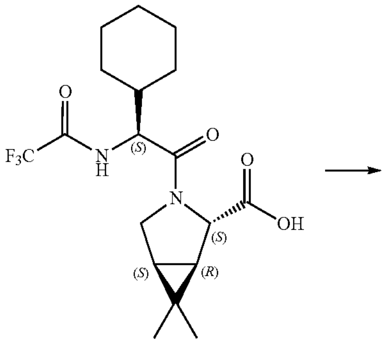
1B-5
-continued
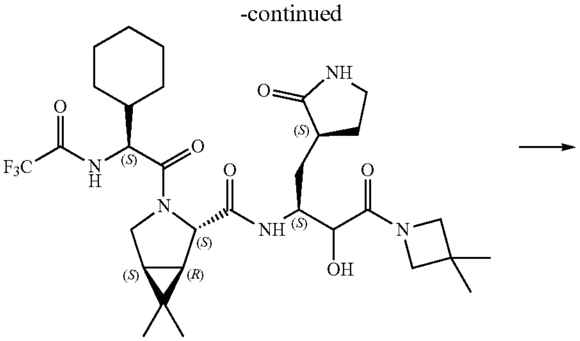
1B-6
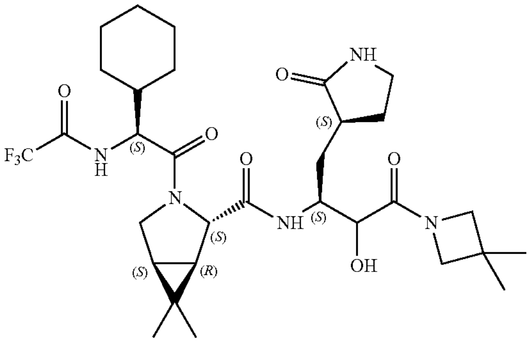
Compound (I-2)
Synthesis and Characterization
methyl (1R,2S,5S)-3-((S)-2-((tert-butoxycarbonyl)amino)-2-cyclohexylacetyl)-6,6-dimethyl-3-azabicyclo[3.1.0]hexane-2-carboxylate
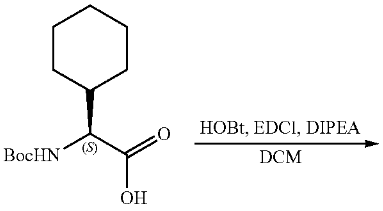
1B-1
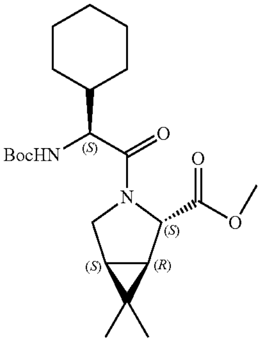
1B-2
A round-bottom flask was charged with(S)-2-((tert-butoxycarbonyl)amino)-2-cyclohexylacetic acid (1 g, 3.89 mmol), DCM (10 mL), HOBt (420.1 mg, 3.11 mmol), EDCl(744.9 mg, 3.89 mmol) and DIPEA(1.51 g, 11.66 mmol), methyl (1S,2S,5R)-6,6-dimethyl-3-azabicyclo [3.1.0]hexane-2-carboxylate (657.61 mg, 3.89 mmol) was added, The reaction mixture was stirred at rt for 12 h. The mixture was quenched with 10 mL, extracted with DCM (10 mL×2), separated, dried, concentrated by rotary evaporation and purified directly by silica gel chromatography eluting with PE/EtOAc (9:1) to give methyl(1R,2S,5S)-3-((S)-2-((tert-butoxycarbonyl)amino)-2-cyclohexylacetyl)-6,6-dimethyl-3-azabicyclo[3.1.0]hexane-2-carboxylate (1 g, yield: 62.9%) as yellow oil. MS (ESI): m/z 353.6 [M−55]+.

methyl (1R,2S,5S)-3-((S)-2-amino-2-cyclohexylacetyl)-6,6-dimethyl-3-azabicyclo[3.1.0]hexane-2-carboxylate

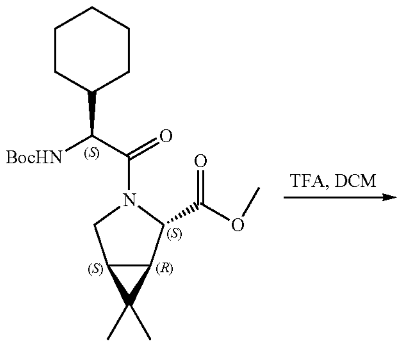

1B-2

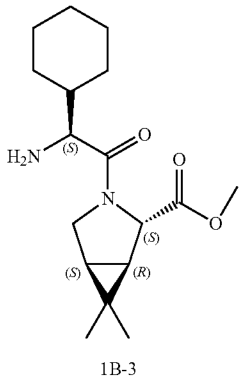

1B-3

To methyl (1R,2S,5S)-3-((S)-2-((tert-butoxycarbonyl) amino)-2-cyclohexylacetyl)-6,6-dimethyl-3-azabicyclo [3.1.0]hexane-2-carboxylate (1 g, 2.45 mmol) in DCM (10 mL), and TFA(10 mL) was added. The mixture was stirred at rt for 16 hours under $N_2$, the mixture was concentrated to afford the methyl (1R,2S,5S)-3-((S)-2-amino-2-cyclohexylacetyl)-6,6-dimethyl-3azabicyclo[3.1.0]hexane-2-carboxylate.TFA salt (1.03 g, yield: 100%), MS (ESI): m/z 309.2 $[M+H]^+$.

methyl (1R,2S,5S)-3-(S)-2-cyclohexyl-2-(2,2,2-trifluoroacetamido)acetyl)-6,6-dimethyl-3-azabicyclo [3.1.0]hexane-2-carboxylate

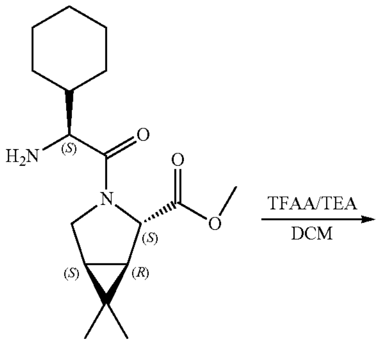

1B-3

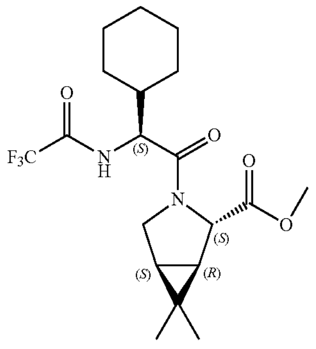

1B-4

To a solution methyl (1R,2S,5S)-3-(S)-2-amino-2-cyclohexylacetyl)-6,6-dimethyl-3-azabicyclo[3.1.0]hexane-2-carboxylate.TFA salt (1.03 g, 2.44 mmol) in DCM(10 ml), EtOAc (1.48 g, 14.63 mmol), and TFAA (768.14 mg, 3.66 mmol) was added. The reaction was stirred at rt for 2 h. the mixture was concentrated to get the crude and purified directly by silica gel chromatography eluting with PE/EtOAc (5:1) to give methyl (1R,2S,5S)-3-((S)-2-cyclohexyl-2-(2,2,2-trifluoroacetamido)acetyl)-6,6-dimethyl-3-azabicyclo[3.1.0]hexane-2-carboxylate (400 mg, yield: 40.6%) as yellow oil. MS (ESI): m/z 405.6 $[M+H]^+$.

(1R,2S,5S)-3-((S)-2-cyclohexyl-2-(2,2,2-trifluoroacetamido)acetyl)-6,6-dimethyl-3-azabicyclo[3.1.0] hexane-2-carboxylic acid

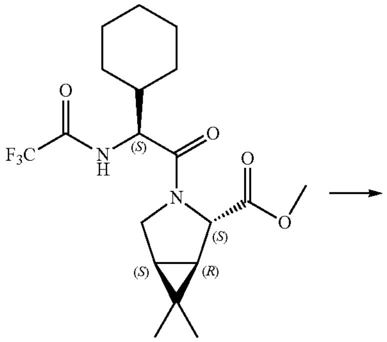

1B-4

-continued

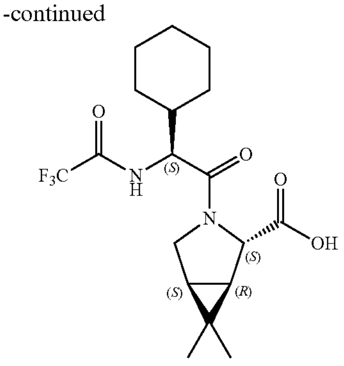

1B-5

To a solution of methyl (1R,2S,5S)-3-((S)-2-cyclohexyl-2-(2,2,2-trifluoroacetamido)acetyl)-6,6-dimethyl-3-azabicyclo[3.1.0]hexane-2-carboxylate (400 mg, 0.89 mmol) in THF (1 mL) and $H_2O$ (1 mL), $LiOH{\cdot}H_2O$ (83 mg, 1.98 mmol) was added, the mixture was stirred at for 16 h, the mixture was adjusted pH to 4 with 1N HCl, extracted with EtOAc(10 mL×2), separated, dried, concentrated in vacuo to give the (1R,2S,5S)-3-((S)-2-cyclohexyl-2-(2,2,2-trifluoroacetamido) acetyl)-6,6-dimethyl-3-azabicyclo[3.1.0]hexane-2-carboxylic acid (300 mg, 77.7% yield) as a white solid: MS (ESI): m/z 391.5 $[M+H]^+$.

(1R,2S,5S)-3-((S)-2-cyclohexyl-2-(2,2,2-trifluoroacetamido)acetyl)-N-((2S)-4-(3,3-dimethylazetidin-1-yl)-3-hydroxy-4-oxo-1-((S)-2oxopyrrolidin-3-yl) butan-2-yl)-6,6-dimethyl-3-azabicyclo[3.1.0]hexane-2-carboxamide

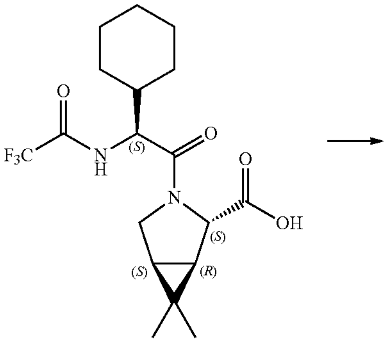

1B-5

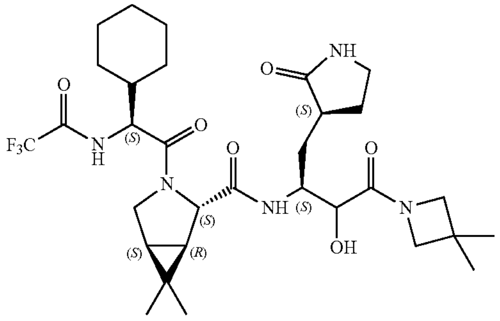

1B-6

A round-bottom flask was charged with (1R,2S,5S)-3-((S)-2-cyclohexyl-2-(2,2,2-trifluoroacetamido)acetyl)-6,6-dimethyl-3-azabicyclo[3.1.0]hexane-2-carboxylic acid (240 mg, 0.61 mmol), DCM (5 mL), HOBt (83.1 mg, 0.61 mmol), EDCl(176.7 mg, 0.92 mmol) and DIPEA(476.7 mg, 3.69 mmol), then tert-butyl (2S)-4-(3,3-dimethylazetidin-1-yl)-3-hydroxy-4-oxo-1-((S)-2-oxopyrrolidin-3-yl) butan-2-yl)carbamate (227.1 mg, 0.61 mmol) was added, The reaction mixture was stirred at rt for 12 h. The mixture was purified by reverse phase column chromatography eluted with water ($NH_4HCO_3$)/acetonitrile=70:30 to give (1R,2S,5S)-3-((S)-2-cyclohexyl-2-(2,2,2-trifluoroacetamido)acetyl)-N-((2-S) 4-(3,3-dimethylazetidin-1-yl)-3-hydroxy-4-oxo-1-((S)-2-oxopyrrolidin-3-yl)butan-2-yl)-6,6-dimethyl-3-azabicyclo [3.1.0]hexane-2-carboxamide (150 mg, yield: 38.1%) as white solid. MS (ESI): m/z 642.8 $[M+H]^+$.

(1R,2S,5S)-3-((S)-2-cyclohexyl-2-(2,2,2-trifluoroacetamido)acetyl)-N—((S)-4-(3,3-dimethylazetidin-1-yl)-3,4-dioxo-1-((S)-2-oxopyrrolidin-3-yl)butan-2-yl)-6,6-dimethyl-3-azabicyclo[3.1.0]hexane-2-carboxamide

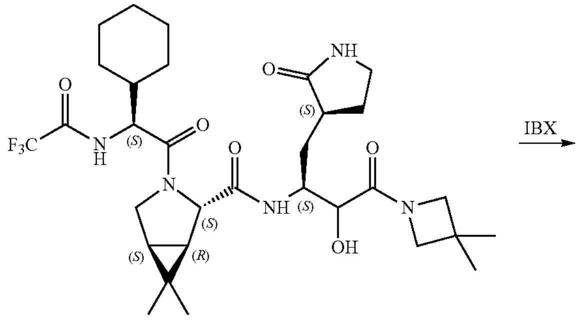

1B-6

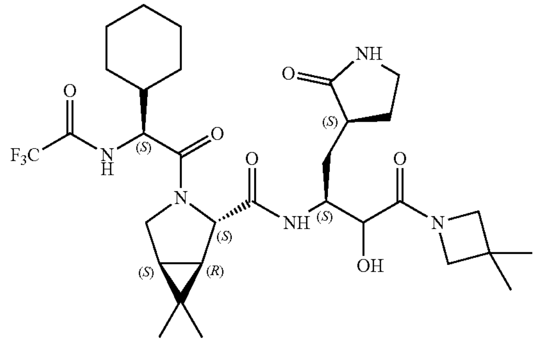

Compound (I-2)

To a solution of (1R,2S,5S)-3-((S)-2-cyclohexyl-2-(2,2,2-trifluoroacetamido)acetyl)-N-((2S)-4-(3,3-dimethylazetidin-1-yl)-3-hydroxy-4-oxo-1-((S)-2-oxopyrrolidin-3-yl) butan-2-yl)-6,6-dimethyl-3-azabicyclo[3.1.0]hexane-2-carboxamide (150 mg, 0.23 mmol) in DMSO (2 mL) was added IBX (392 mg, 1.4 mmol), the mixture was stirred at rt for 16 h, the mixture was purified by reverse phase column chromatography eluted with water (10 mol/L, $NH_4HCO_3$)/acetonitrile=70:30 to get (1R,2S,5S)-3-((S)-2-cyclohexyl-2-(2,2,2-trifluoroacetamido)acetyl)-N—((S)-4-(3,3-dimethylazetidin-1-yl)-3,4-dioxo-1-((S)-2-oxopyrrolidin-3-yl)butan-2-yl)-6,6-dimethyl-3-azabicyclo[3.1.0]hexane-2-carboxamide as a white solid (52.2 mg, yield: 34.9%).

Example 1C—Illustrative Synthesis of a Compound of Formula (1-4)
(I-4)
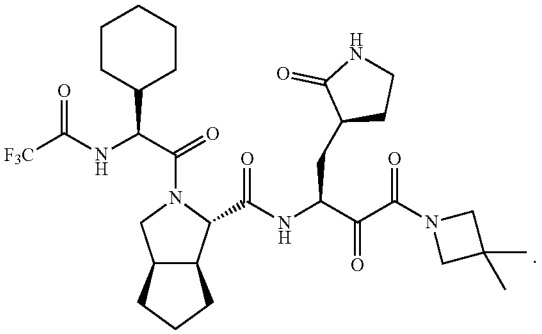
The following synthetic scheme was followed to provide compound (1-4).
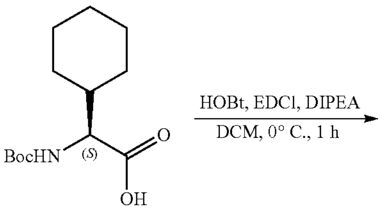
1C-1
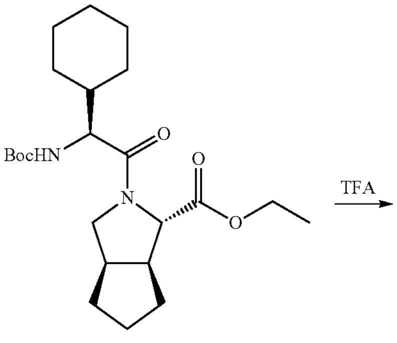
1C-2
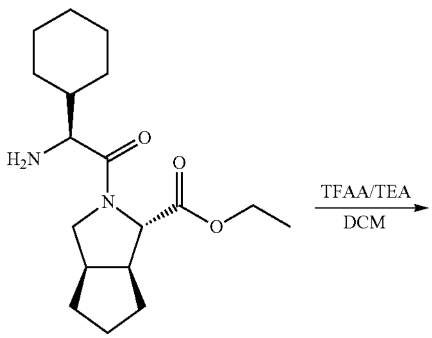
1C-3
-continued
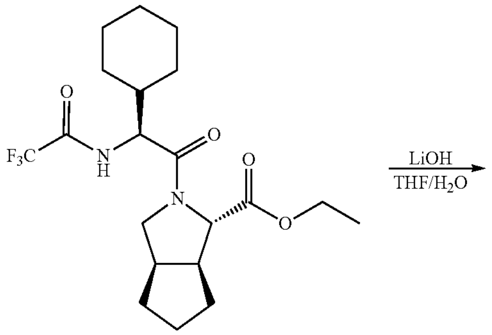
1C-4
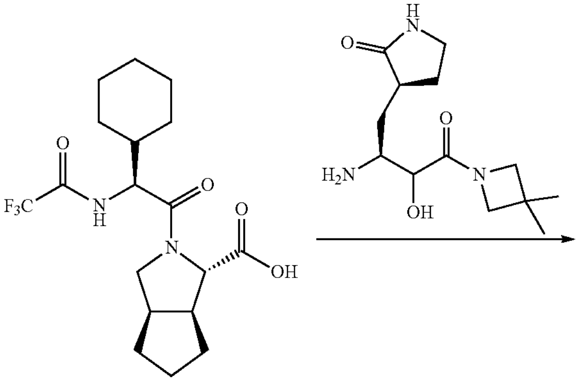
1C-5
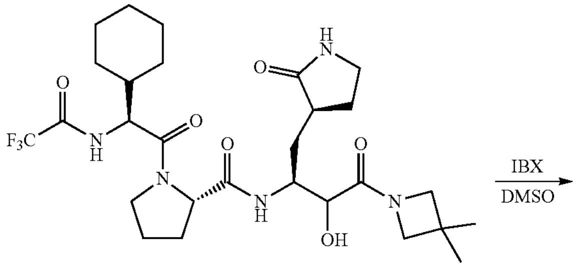
1C-6
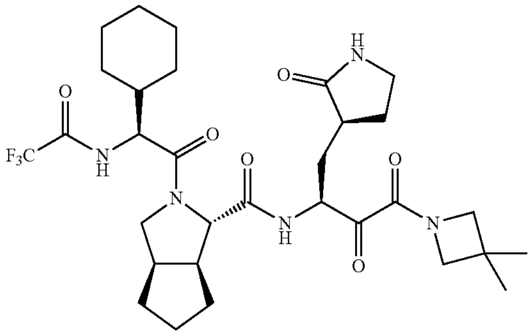
Compound (I-4)

Synthesis and Characterization

Ethyl (1S,3aR,6aS)-2-((S)-2-((tert-butoxycarbonyl)amino)-2-cyclohexylacetyl)octahydrocyclopenta[c]pyrrole-1-carboxylate (1C-2)

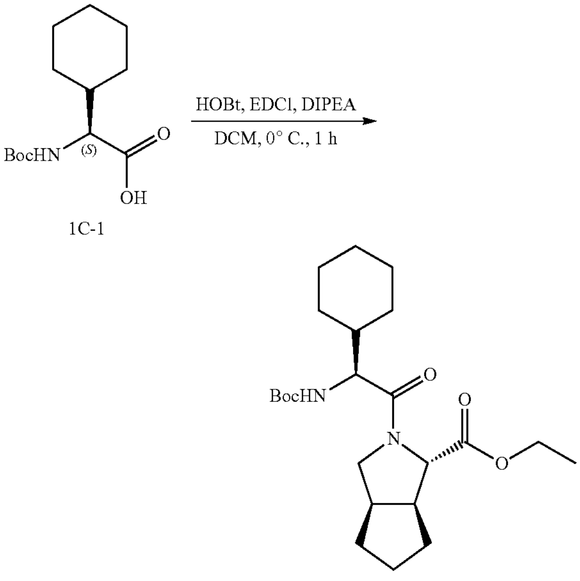

1C-1

1C-2

To a solution of(S)-2-((tert-butoxycarbonyl)amino)-2-cyclohexylacetic acid (3 g, 11.67 mmol, 1.0 eq.) in DCM(50 mL) were added HOBT (3.15 g, 23.34 mmol, 2.0 eq.), EDCl (3.35 g, 17.50 mmol, 1.5 eq.), DIPEA (5.7 mL, 35.01 mmol, 3 eq.), ethyl (1S,3aR,6aS)-octahydrocyclopenta[c]pyrrole-1-carboxylate hydrochloride (3.07 g, 14.01 mmol, 1.2 eq.). The mixture was stirred at 0° C. for 1 h. The reaction mixture was added water (50 mL), then was extracted DCM (30 mL×3), wash with brine (50 mL), the orange layer was dried over anhydrous $Na_2SO_4$. The reaction was concentrated by rotary evaporation under reduced pressure to give a residue. The residue was purified by column chromatography on silica gel (EtOAc in petroleum ether from 0%~20%) to afford ethyl (1S,3aR,6aS)-2-((S)-2-((tert-butoxycarbonyl)amino)-2-cyclohexylacetyl)octahydrocyclopenta[c]pyrrole-1-carboxylate as colourless gum. (4.1 g, 83.2% yield). MS (ESI): m/z 223 $[M+H]^+$.

Ethyl (1S,3aR,6aS)-2-((S)-2-amino-2-cyclohexylacetyl)octahydrocyclopenta[c]pyrrole-1-carboxylate (1C-3)

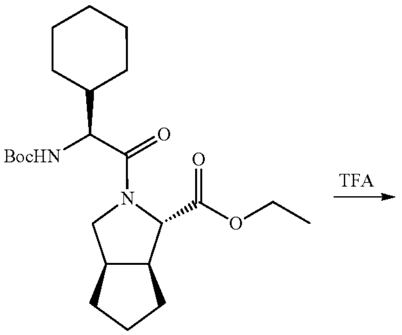

1C-2

-continued

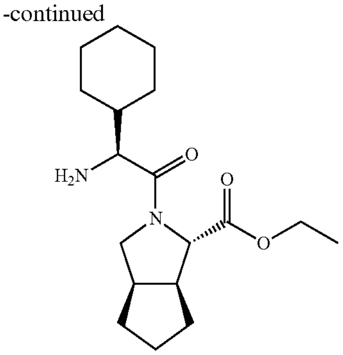

1C-3

To a solution of ethyl (1S,3aR,6aS)-2-((S)-2-((tert-butoxycarbonyl)amino)-2-cyclohexylacetyl) octahydrocyclopenta[c]pyrrole-1-carboxylate (4.1 g, 10.05 mmol, 1.0 eq.) in DCM (50 mL) was added trifluoroacetic acid (5 mL) at room temperature. Then the mixture was stirred at this temperature for 2 h. After concentration, the residue was used for next step with further purification. Ethyl (1S,3aR,6aS)-2-((S)-2-amino-2-cyclohexylacetyl)octahydrocyclopenta[c]pyrrole-1-carboxylate (3.2 g, crude) was obtained. MS (ESI): m/z=323.0 $[M+H]^+$.

ethyl (1S,3aR,6aS)-2-((S)-2-cyclohexyl-2-(2,2,2-trifluoroacetamido)acetyl)octahydrocyclopenta[c]pyrrole-1-carboxylate (1C-4)

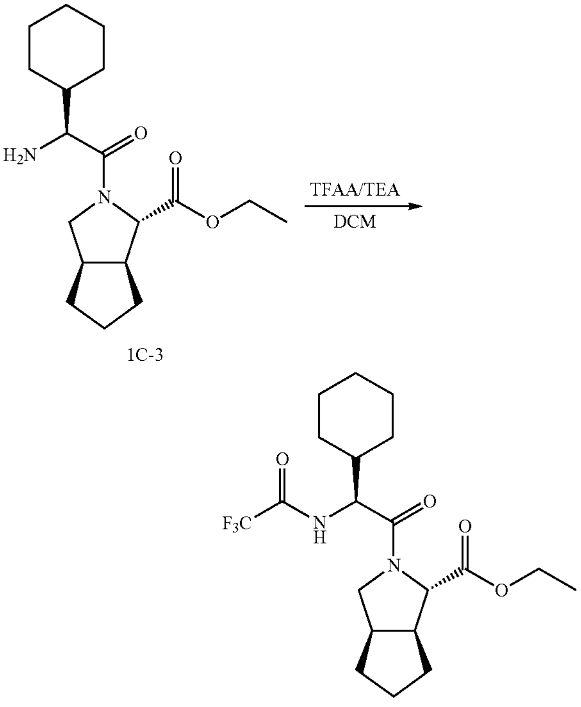

1C-3

1C-4

To a solution of ethyl (1S,3aR,6aS)-2-((S)-2-amino-2-cyclohexylacetyl)octahydrocyclopenta[c]pyrrole-1-carboxylate (3.2 g, 9.94 mmol, 1.0 eq.) in DCM (20 mL) was added triethylamine (2 g, 19.87 mmol, 2.0 eq.) and trifluoroacetic anhydride (3.13 g, 14.91 mmol, 1.5 eq.) at 0° C. Then the mixture was stirred at room temperature for 1 h. Water (20 mL) was added to the mixture and the mixture was extracted with DCM (3×20 mL). The organics were dried, filtrated and concentrated to get ethyl (1S,3aR,6aS)-2-((S)-2-cyclohexyl-2-(2,2,2-trifluoroacetamido)acetyl)octahydrocyclopenta[c]pyrrole-1-carboxylate as a yellow gum (2.8 g, crude). MS (ESI): m/z 419 [M+H]+.

(1S,3aR,6aS)-2-((S)-2-cyclohexyl-2-(2,2,2-trifluoroacetamido)acetyl)octahydrocyclopenta[c]pyrrole-1-carboxylic acid (1C-5)

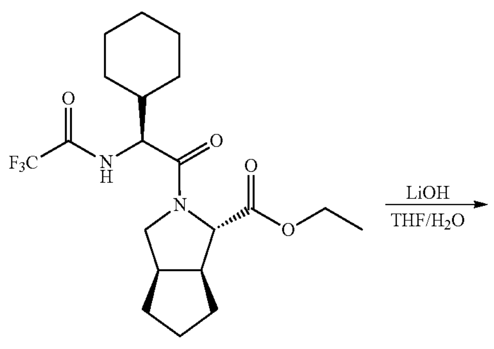

1C-4

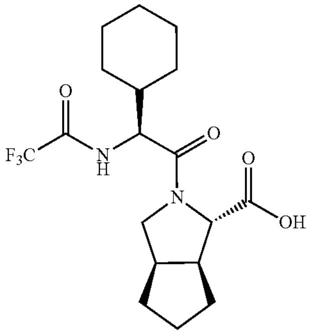

1C-5

To a solution of ethyl (1S,3aR,6aS)-2-((S)-2-cyclohexyl-2-(2,2,2-trifluoroacetamido)acetyl) octahydrocyclopenta[c]pyrrole-1-carboxylate (2.8 g, 6.7 mmol, 1.0 eq.) in THF (20 mL) was added lithium hydroxide (338 mg, 8.04 mmol, 1.2 eq.) in $H_2O$ (5 mL) at room temperature. Then the mixture was stirred at this temperature for 12 h. Upon the completion, the mixture was adjusted to pH=6 with 2N HCl solution and the mixture was extracted with DCM (3×50 mL). The organics were dried, filtrated and concentrated. The residue was purified by preparative HPLC, and dried by lyophilized to give (1S,3aR,6aS)-2-((S)-2-cyclohexyl-2-(2,2,2-trifluoroacetamido)acetyl)octahydrocyclopenta[c]pyrrole-1-carboxylic acid as a white solid (400 mg, yield: 15%). MS (ESI): m/z 390.9 [M+H]+.

(1S,3aR,6aS)-2-((S)-2-cyclohexyl-2-(2,2,2-trifluoroacetamido)acetyl)-N-((2S)-4-(3,3-dimethylazetidin-1-yl)-3-hydroxy-4-oxo-1-((S)-2-oxopyrrolidin-3-yl)butan-2-yl)octahydrocyclopenta[c]pyrrole-1-carboxamide (1C-6)

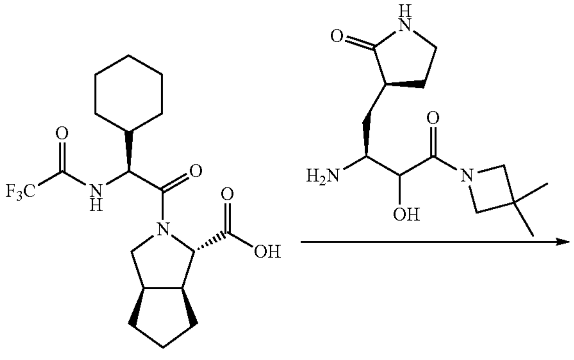

1C-5

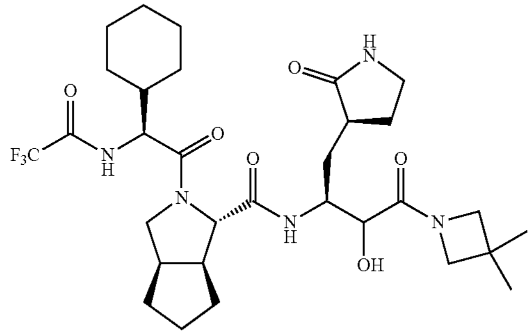

1C-6

To a solution of (1S,3aR,6aS)-2-((S)-2-cyclohexyl-2-(2,2,2-trifluoroacetamido)acetyl)octahydrocyclopenta[c]pyrrole-1-carboxylic acid (400 mg, 1.03 mmol, 1.0 eq.) in DMF (10 mL) were added (3S)-3-amino-N-cyclopentyl-2-hydroxy-4-((S)-2-oxopyrrolidin-3-l)butanamide (331 mg, 1.23 mmol, 1.2 eq.), 1-ethyl-3-(3-dimethylaminopropyl) carbodiimide hydrochloride (295 mg, 1.55 mmol, 1.5 eq.), HOBT (278 mg, 2.06 mmol, 2.0 eq.) and N, N-diisopropylethylamine (0.51 mL, 3.09 mmol, 3.0 eq.) at room temperature. Then the mixture was stirred at this temperature for 16 h. The residue was purified by prep-HPLC with water (0.05% aq. trifluoroacetic acid)/acetonitrile=70:30 and dried by lyophilized to give (1S,3aR,6aS)-2-((S)-2-cyclohexyl-2-(2,2,2-trifluoroacetamido) acetyl)-N-((2S)-4-(3,3-dimethylazetidin-1-yl)-3-hydroxy-4-oxo-1-((S)-2-oxopyrrolidin-3-yl) butan-2-yl)octahydrocyclopenta[c]pyrrole-1-carboxamide as a white solid (251 mg, yield: 38.3%). MS (ESI): m/z 641.9 [M+H]+.

(1S,3aR,6aS)-2-((S)-2-cyclohexyl-2-(2,2,2-trifluoro-acetamido) acetyl)-N—((S)-4-(3,3-dimethylazetidin-1-yl)-3,4-dioxo-1-((S)-2-oxopyrrolidin-3-yl)butan-2-yl)octahydrocyclopenta[c]pyrrole-1-carboxamide (1-4)

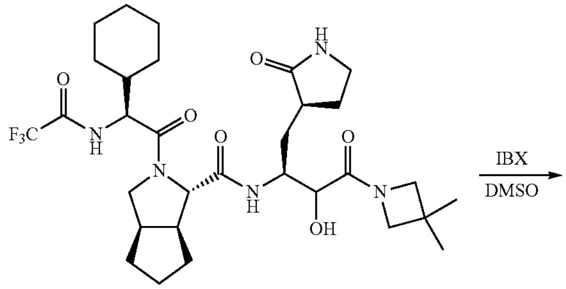

1C-6

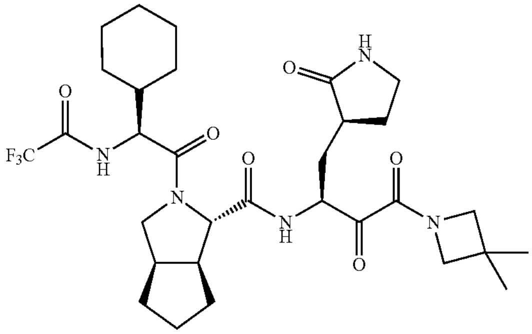

Compound (I-4)

To a solution of (1S,3aR,6aS)-2-((S)-2-cyclohexyl-2-(2,2,2-trifluoroacetamido)acetyl)-N-((2S)-4-(3,3-dimethylazetidin-1-yl)-3-hydroxy-4-oxo-1-((S)-2-oxopyrrolidin-3-yl) butan-2-yl)octahydrocyclopenta[c]pyrrole-1-carboxamide (95 mg, 0.15 mmol, 1.0 eq.) in dimethyl sulfoxide (4 mL) was added IBX (249 mg, 0.89 mmol, 6.0 eq.) at room temperature. Then the mixture was stirred at this temperature for 8 h. The residue was purified prep-HPLC with water (0.05% aq. trifluoroacetic acid)/acetonitrile=70:30, and dried by lyophilized to give (1S,3aR,6aS)-2-((S)-2-cyclohexyl-2-(2,2,2-trifluoroacetamido) acetyl)-N—((S)-4-(3,3-dimethylazetidin-1-yl)-3,4-dioxo-1-((S)-2-oxopyrrolidin-3-yl)butan-2-yl)octahydrocyclopenta[c]pyrrole-1-carboxamide as a white solid (71.9 mg, yield: 76.5%).

Example 1D—Illustrative Synthesis of a Compound of Formula (II)

compound (II)

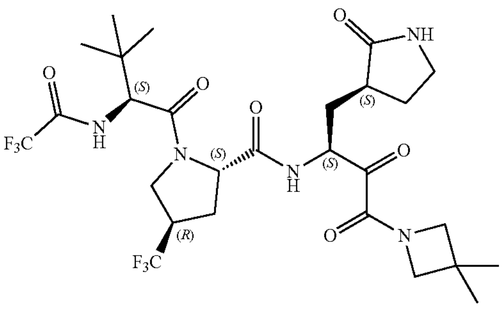

Scheme S1: Synthetic Route for Compound (II).

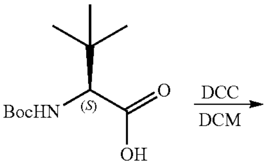

1D-1

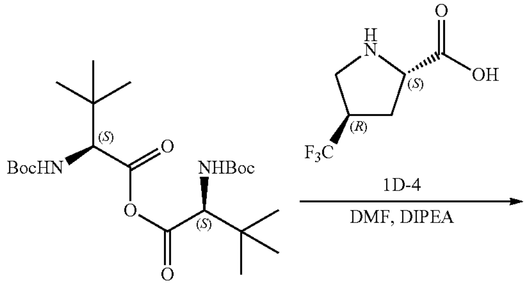

1D-2

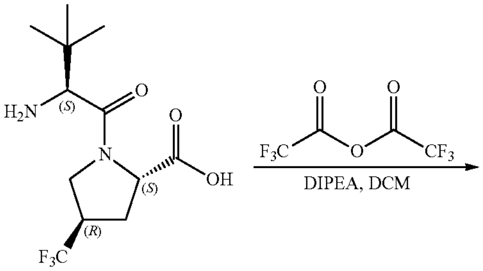

1D-5

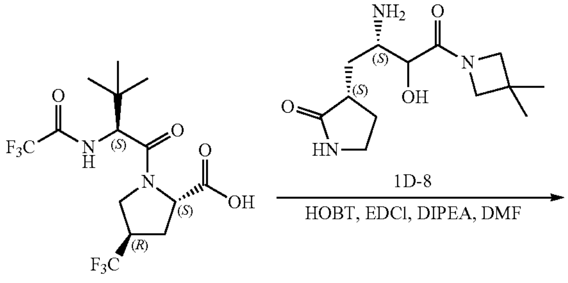

1D-6

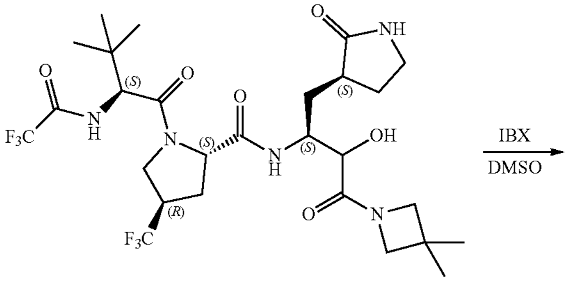

1D-9

-continued

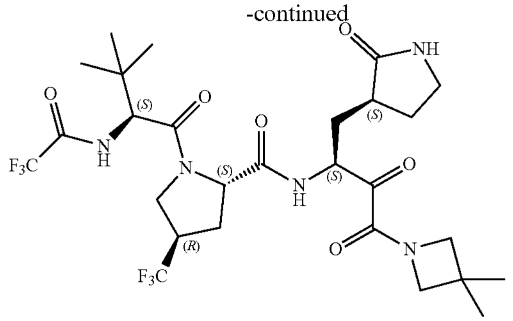

Compound (II)

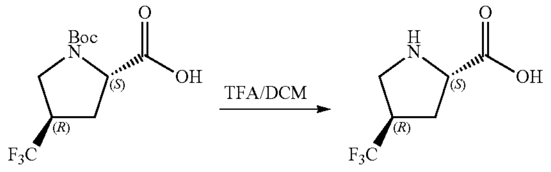

1D-3 1D-4

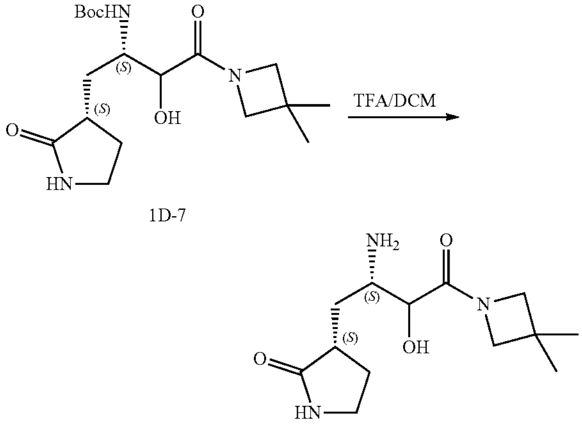

1D-7

1D-8

Synthesis and Characterization

(S)-2-((tert-butoxycarbonyl)amino)-3,3-dimethylbutanoic anhydride (1D-2)

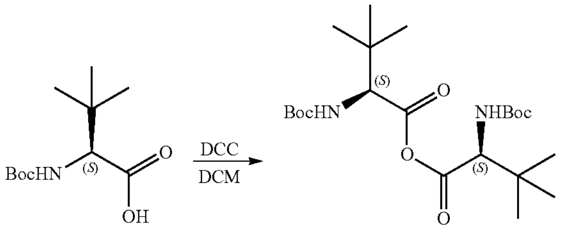

1D-1 1D-2

To a solution of(S)-2-((tert-butoxycarbonyl)amino)-3,3-dimethylbutanoic acid (10.0 g, 43.2 mmol, 1.0 eq.) in DCM (200 ml) was added DCC (4.46 g, 21.6 mmol, 0.5 eq) at 25° C. Then the mixture was stirred at this temperature for 16 h. The reaction was filtered and the filtrate was concentrated in vacuo to afford(S)-2-((tert-butoxycarbonyl)amino)-3,3-dimethylbutanoic anhydride (10 g, crude) as a colorless oil. MS (ESI): m/z 467 $[M+23]^+$.

(2S,4R)-4-(trifluoromethyl)pyrrolidine-2-carboxylic acid (1D-4)

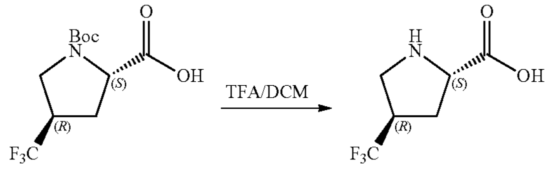

1D-3 1D-4

To a solution of (2S,4R)-1-(tert-butoxycarbonyl)-4-(trifluoromethyl)pyrrolidine-2-carboxylic acid (1.5 g, 5.3 mmol, 1.0 eq.) in DCM (30 mL) was added TFA (10 mL) at 25° C. Then the mixture was stirred at 25° C. for 1 h. The reaction was concentrated in vacuo to afford (2S,4R)-4-(trifluoromethyl)pyrrolidine-2-carboxylic acid (1.5 g, crude) as a colorless oil. MS (ESI): m/z 184 $[M+H]^+$.

(2S,4R)-1-((S)-2-amino-3,3-dimethylbutanoyl)-4-(trifluoromethyl)pyrrolidine-2-carboxylic acid (1D-5)

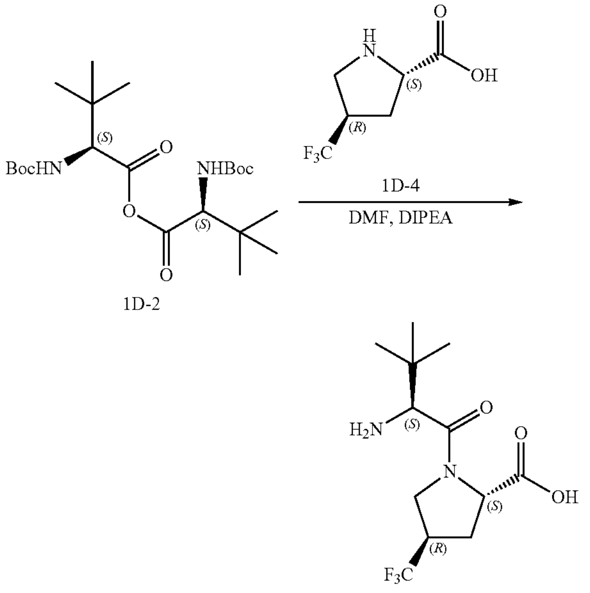

1D-2

1D-5

To a solution of(S)-2-((tert-butoxycarbonyl)amino)-3,3-dimethylbutanoic anhydride (3 g, 6.8 mmol) in DMF (20 mL) was added (2S,4R)-4-(trifluoromethyl)pyrrolidine-2-carboxylic acid (1.5 g, 5.1 mmol, 0.75 eq.) and DIPEA (5.9 mL, 33.7 mmol). Then the mixture was stirred at 25° C. for 1 h. The reaction was purified by Prep-HPLC (A:water(10 mM $NH_4HCO_3$), B:acetonitrile, 10-30% B in 9 min) to afford (2S,4R)-1-((S)-2-amino-3,3-dimethylbutanoyl)-4-(trifluoromethyl) pyrrolidine-2-carboxylic acid (1 g, 49%) as a white solid. MS (ESI): m/z 297 $[M+1]^+$.

(2S,4R)-1-((S)-3,3-dimethyl-2-(2,2,2-trifluoroacetamido)butanoyl)-4-(trifluoromethyl)pyrrolidine-2-carboxylic acid (1D-6)

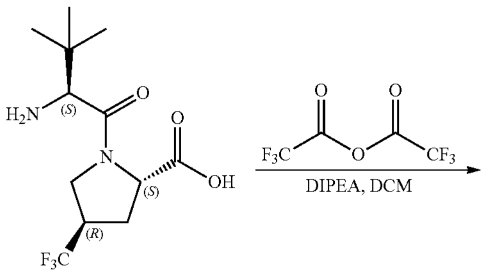

1D-5

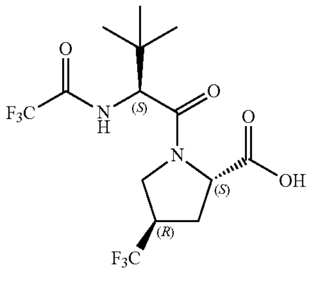

1D-6

To a solution of (2S,4R)-1-((S)-2-amino-3,3-dimethylbutanoyl)-4-(trifluoromethyl) pyrrolidine-2-carboxylic acid (1 g, 3.4 mmol) in DCM (30 mL) was added 2,2,2-trifluoroacetic anhydride (0.94 mL, 6.8 mmol, 2.0 eq.) and DIPEA (2.4 mL, 13.5 mmol, 4.0 eq.) at 0° C. Then the mixture was stirred at 0° C. for 2 h. The reaction was concentrated in vacuo and the residue was purified by prep-HPLC (A: water (10 mM $NH_4HCO_3$), B:acetonitrile, 20-37% B in 9 min) to afford (2S,4R)-1-((S)-3,3-dimethyl-2-(2,2,2-trifluoroacetamido)butanoyl)-4-(trifluoromethyl)pyrrolidine-2-carboxylic acid (100 mg, yield: 7.5%) as a white solid. MS (ESI): m/z 393 $[M+1]^+$.

(3S)-3-((2S)-2-amino-4-(3,3-dimethylazetidin-1-yl)-3-hydroxy-4-oxobutyl)pyrrolidin-2-one (1D-8)

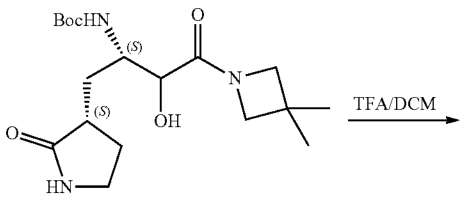

1D-7

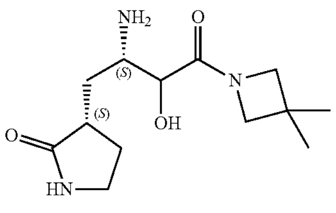

1D-8

To a solution of tert-butyl ((2S)-4-(3,3-dimethylazetidin-1-yl)-3-hydroxy-4-oxo-1-((S)-2-oxopyrrolidin-3-yl)butan-2-yl)carbamate (0.15 g, 0.41 mmol, 1.0 eq.) in DCM (6 mL) was added TFA (2 ml) at 0° C. Then the mixture was stirred at this temperature for 2 h. The reaction was concentrated in vacuo to afford (3S)-3-((2S)-2-amino-4-(3,3-dimethylazetidin-1-yl)-3-hydroxy-4-oxobutyl)pyrrolidin-2-one (150 mg, crude) as a colorless oil. MS (ESI): m/z 270 $[M+H]^+$.

(2S,4R)-1-((S)-3,3-dimethyl-2-(2,2,2-trifluoroacetamido)butanoyl)-N-(2S)-4-(3,3-dimethylazetidin-1-yl)-3-hydroxy-4-oxo-1-((S)-2-oxopyrrolidin-3-yl) butan-2-yl)-4-(trifluoromethyl)pyrrolidine-2-carboxamide (1D-9)

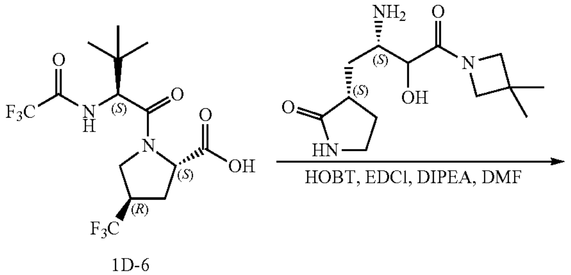

1D-6

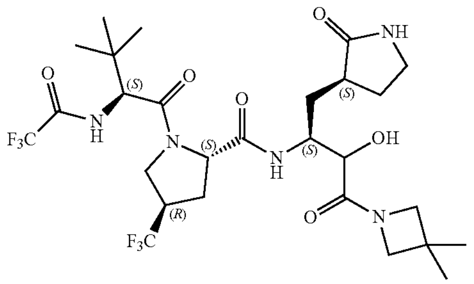

1D-9

To a solution of (2S,4R)-1-((S)-3,3-dimethyl-2-(2,2,2-trifluoroacetamido)butanoyl)-4-(trifluoromethyl)pyrrolidine-2-carboxylic acid (100 mg, 0.25 mmol, 1.0 eq.) in DMF (5 mL) was added (3S)-3-((2S)-2-amino-4-(3,3-dimethylazetidin-1-yl)-3-hydroxy-4-oxobutyl)pyrrolidin-2-one (1D-8) (150 mg, 0.41 mmol, 1.6 eq.), HOBT (38 mg, 0.28 mmol, 1.1 eq.), EDCl (73 mg, 0.38 mmol, 1.5 eq.) and DIPEA (0.22 mL, 1.27 mmol, 5 eq.). Then the mixture was stirred at 25° C. for 16 h. The reaction was purified by prep-HPLC (A: water (10 mM $NH_4HCO_3$), B:acetonitrile, 20-55% B in 9 min) to afford (2S,4R)-1-((S)-3,3-dimethyl-2-(2,2,2-trifluoroacetamido)butanoyl)-N-((2S)-4-(3,3-dimethylazetidin-1-yl)-3-hydroxy-4-oxo-1-((S)-2-oxopyrrolidin-3-yl)butan-2-yl)-4-(trifluoromethyl)pyrrolidine-2-carboxamide as a white solid (50 mg, yield: 30%). MS (ESI): m/z 644 $[M+H]^+$.

(2S,4R)-1-((S)-3,3-dimethyl-2-(2,2,2-trifluoroacetamido) butanoyl)-N—((S)-4-(3,3-dimethylazetidin-1-yl)-3,4-dioxo-1-((S)-2-oxopyrrolidin-3- yl)butan-2-yl)-4-(trifluoromethyl)pyrrolidine-2-carboxamide (Compound (II))

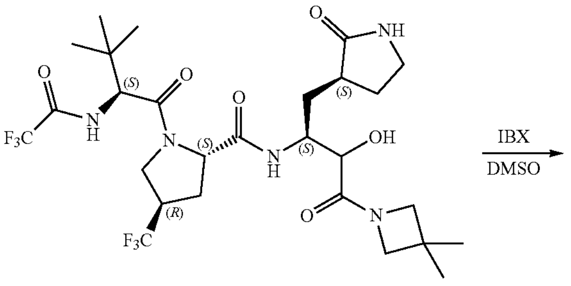

1D-9

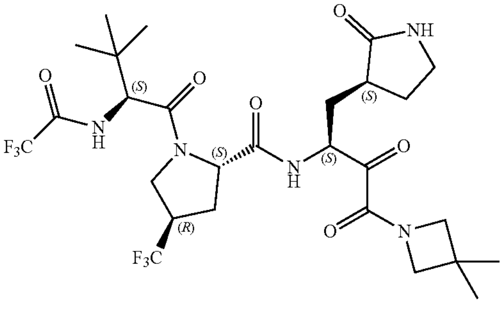

Compound (II)

To a solution of (2S,4R)-1-((S)-3,3-dimethyl-2-(2,2,2-trifluoroacetamido)butanoyl)-N-((2S)-4-(3,3-dimethylazetidin-1-yl)-3-hydroxy-4-oxo-1-((S)-2-oxopyrrolidin-3-yl)butan-2-yl)-4-(trifluoromethyl)pyrrolidine-2-carboxamide (50 mg, 0.078 mmol, 1.0 eq.) in dimethyl sulfoxide (3 mL) was added IBX (130 mg, 0.47 mmol, 6.0 eq.) at 25° C. Then the mixture was stirred at this temperature for 16 h. The mixture was purified by prep-HPLC (A:water(10 mM $NH_4HCO_3$), B:acetonitrile, 5-25% B in 9 min) to get (2S,4R)-1-((S)-3,3-dimethyl-2-(2,2,2-trifluoroacetamido)butanoyl)-N—((S)-4-(3,3-dimethylazetidin-1-yl)-3,4-dioxo-1-((S)-2-oxopyrrolidin-3-yl) butan-2-yl)-4-(trifluoromethyl)pyrrolidine-2-carboxamide as a white solid (5 mg, yield: 10%).

Example 1E—$^1$H NMR and MS Data for Compounds (I-1), (I-2), (I-3), (1-4) and (II)

| Compound | $^1$H NMR data at room temperature |
|---|---|
| (I-1) | (400 MHz, DMSO-d6) δ: 9.93-7.19 (m, 3H), 5.02-4.74 (m, 1H), 4.29-3.90 (m, 4H), 3.88-3.39 (m, 4H), 3.14-3.02 (m, 2H), 2.38-1.90 (m, 4H), 1.77-1.17 (m, 12H), 1.06-0.80 (m, 12H). (400 MHz, $CDCl_3$) δ: 9.15-7.95 (m, 1H), 7.16-6.92 (m, 1H), 5.96-5.72 (m, 1H), 5.14-4.79 (m, 1H), 4.60-4.47 (m, 1H), 4.39-4.29 (m, 1H), 4.24-3.56 (m, 6H), 3.38-3.24 (m, 2H), 2.76-1.74 (m, 7H), 1.62-1.44 (m, 3H), 1.32-1.24 (m, 6H), 1.09-0.80 (m, 12H). |
| (I-2) | (400 MHz, DMSO-d6) δ: 9.86-7.43 (m, 3H), 4.99-3.41 (m, 9H), 3.20-3.02 (m, 2H), 2.49-2.31 (m, 1H), 2.19-2.05 (m, 1H), 1.96-1.43 (m, 10H), 1.29-0.83 (m, 18H). (400 MHz, $CDCl_3$) δ: 9.19-8.08 (m, 1H), 7.19-7.03 (m, 1H), 5.76-5.55 (m, 1H), 5.13-4.84 (m, 1H), 4.56-4.24 (m, 2H), 4.19-3.56 (m, 6H), 3.49-3.30 (m, 2H), 2.93-2.42 (m, 2H), 2.26-1.76 (m, 6H), 1.63-1.42 (m, 4H), 1.33-0.82 (m, 18H). |
| (I-3) | (500 MHz, DMSO-d6) δ: 9.79-7.39 (m, 3H), 4.88-3.55 (m, 9H), 3.20-2.96 (m, 2H), 2.73-2.63 (m, 1H), 2.48-2.09 (m, 5H), 1.97-1.34 (m, 15H), 1.17-0.86 (m, 5H). |
| (I-4) | (400 MHz, DMSO-d6) δ: 9.88-7.38 (m, 3H), 4.95-3.40 (m, 9H), 3.20-2.95 (m, 2H), 2.74-2.60 (m, 1H), 2.47-2.07 (m, 3H), 2.01-1.32 (m, 15H), 1.27-0.82 (m, 11H). |
| (II) | (400 MHz, $CDCl_3$) δ: 9.90-8.35 (m, 1H), 6.98-6.90 (m, 1H), 5.67-5.54 (m, 1H), 5.12-4.74 (m, 1H), 4.71-4.37 (m, 2H), 4.19-3.91 (m, 3H), 3.86-3.66 (m, 3H), 3.50-2.99 (m, 3H), 2.60-1.83 (m, 7H), 1.32-1.25 (m, 6H), 1.13-0.90 (m, 9H). |

| Compound | Expected Mass | MS (ESI) m/z [M+H]+ |
|---|---|---|
| (I-1) | 613.3 | 614.3 |
| (I-2) | 639.3 | 640.3 |
| (I-3) | 611.3 | 612.0 |
| (I-4) | 639.3 | 639.8 |
| (II-1) | 641.3 | 642.3 |

Example 2—In Vitro Inhibitor Potency Against $M^{pro}$-coil

Using a synthetic gene of SARS-CoV-2 $M^{pro}$ from the Wuhan strain, His6-SUMO-$M^{pro}$-coil fusion proteins were cloned into a pET vector and used for protein expression. Both a wild-type variant of the SARS-CoV-2 $M^{pro}$-coil and a E166V mutant of $M^{pro}$ were purified. The E166V $M^{pro}$ mutation is known to cause resistance towards Nirmatrelvir. The coil domain fused via a flexible linker forms a parallel homodimer. Thus, the coil fusion facilitates the trapping of $M^{pro}$ in its active dimeric form via avidity effects. This allows improved assay sensitivity and accuracy for determine $K_i$ values of high affinity inhibitors. The fusion protein is produced in full-length and only becomes fully active after SUMO-tag removal during subsequent purification steps.

The plasmids were transformed into T7 Express lysY/$I^q$ *E. coli* cells (New England Biolabs). Small overnight cultures in 2×YT medium with 1% glucose were used to inoculate larger cultures in 2×YT medium that were then grown at 37° C. to $OD_{600}$ of about 0.8 before induction with 0.5 mM IPTG. After induction and 4-5 h growth at room temperature (RT, about 23° C.) the cells were harvested, and the pellets were frozen. Chemical lysis of the resuspended pellets was performed in B-PER (Thermo Scientific) supplemented with 40 U/ml Pierce universal nuclease (Thermo Scientific), and the supernatant cleared by centrifugation at 15000 g for 30 min. The soluble fraction was batch-absorbed onto INDIGO-Ni resin (Cube Biotech) in a buffer containing approximately a combined 45 mM Tris (PH~7.8), 10 mM imidazole, 200 mM NaCl, and 2 mM DTT. The resin was loaded onto gravity flow columns and washed with 20 column volumes of wash buffer containing 50 mM Tris (pH 8.0), 25 mM imidazole, 300 mM NaCl, and 2 mM DTT. High purity protein was eluted in a buffer of 50 mM Tris (pH 8.0), 250 mM imidazole, 300 mM NaCl, and 2 mM DTT. Eluted fractions with high protein content were pooled and buffer exchanged into SUMO protease cleavage buffer (50 mM Tris pH 8.0, 150 mM NaCl, 1 mM DTT). The proteins were cleaved by incubation with 10 U/mg His-tagged SUMO protease (Millipore Sigma SAE0067) by overnight incubation at 4° C. The fully processed $M^{pro}$ variants were then purified using reverse affinity chromatography to remove the His-tagged SUMO proteases and the cleaved $His_6$-tagged fusion-domains. Purity of the samples was checked on SDS-PAGE (>95%), and protein concentrations were determined based on $A_{280}$ and predicted extinction coefficients.

The proteolytic activity of purified $M^{pro}$-coil was measured via the fluorescence intensity increase seen upon cleavage of the fluorogenic peptide, Covidyte TF670 (AAT Bioquest), using a well plate reader (Tecan, Safire 2) with excitation at 640/20 nm and emission at 680/20 nm. All kinetic measurements were performed as bottom-reads from film-covered 96 well plates with clear bottoms. The in-vitro $M^{pro}$ activity was measured in an assay buffer consisting of 50 mM Tris (pH 7.3), 50 mM NaCl, 1 mM EDTA, 3 mM DTT, and 1% DMSO, 0.05% TWEEN20. 60 UL solutions containing 1.5 nM $M^{pro}$(WT) or 7.5 nM $M^{pro}$ (E166V) were preincubated with varying concentrations of inhibitor for 3 h at 37° C. Substrate was added to a final concentration of 3 μM in final volume of 90 μL immediately before initiating the fluorescence readings also at 37° C. The initial rate of substrate cleavage was extracted by linear fitting of the fluorescence signal increase as a function of time. The inhibition curves were plotted as relative proteolytic activity vs. concentration of inhibitor during the preincubation period. Since the inhibitors are preincubated in the absence of substrate and only the initial rate of substrate proteolysis is used in the analysis, the inhibitors have not dissociated from active site and equilibrated with the substrate during fluorescence read-out. Effectively, it was assumed that the substrate does not compete with the $M^{pro}$ inhibitors during the short measurement time of this assay. The apparent equilibrium inhibitor binding constant, $K_{i,app}$, was obtained by non-linear fitting of the Morrison equation while fixing the protein concentration at the preincubated concentration. Furthermore, the concentration of fluorogenic substrate is $<<K_m$=44 μM (obtained in independent experiments). It is thus assumed that $K_i \sim K_{i,app}$. The obtained K, values are tabulated below.

Example 3—Inhibition of Viral Replication

A549-ACE2 ($A549^+$) and Huh7.5.1-ACE2-TMPRSS2 ($Huh7.5.1^{++}$) cells were maintained in D10 growth medium (DMEM, Gibco 11885084) supplemented with 10% FBS (GeminiBio), 2 mM L-glutamine, 10 mM HEPES, 1 mM sodium pyruvate, 1% non-essential amino acids, and 1% antibiotic-antimycotic (all supplements from Gibco)). In addition, the medium was supplemented with 0.5 mg/ml geneticin (Gibco) or 0.2 mg/ml hygromycin (Gibco) for $A549^+$ and $Huh7.5.1^{++}$, respectively. SARS-CoV-2-NLuc (USA-WA1/2020 strain expressing NLuc) virus was passaged twice in Vero E6 cells (ATCC) and titered by plaque assay on Vero E6 cells and confirmed by deep sequencing. The antiviral replication assay was performed in D2 assay medium (D10 medium adjusted to 2% FBS and without antibiotics).

Inhibitors were added in D2 medium to $A549^+$ or $Huh7.5.1^{++}$ cells 24 h after plating the cells in solid white 96-well plates. Control wells were treated with equal concentrations of DMSO. Within 15 min of drug addition, cells were infected with virus at a multiplicity of infection (MOI) of 0.1. After 2 h, the cells were washed with PBS, and followingly incubated with drug for 48 h postinfection (hpi) before addition of lytic Nano-Glo assay (Promega) and reading on a GloMax Discovery plate reader (Promega). The plates always contained a positive inhibition control (e.g., Nirmatrelvir), a DMSO control column as positive infection control, and a column without cells for background signal subtraction. The 10-base logarithm of the luminescent signal was background-corrected and normalized against the DMSO control to represent the relative viral replication rate. The 50% effective antiviral concentration ($EC_{50}$) was obtained by fitting the relative viral replication rate as a function of the inhibitor concentration to a logistic function with adjustable Hill coefficient.

Example 4—Cell Cytotoxicity

Cytotoxicity assays found that none of the tested compounds showed significant toxicity at 100 μM. The protocol for cytotoxicity measurements was as follows: 24 h prior to the inhibitor treatment, 10000 $A549^+$ cells (D10 medium) were seeded in 100 μl culture medium in solid white 96-well plates. The next day, the culture medium was replaced with fresh medium containing inhibitors at the desired concentration (10-100 μM). Staurosporine (0.1 μM or 1 μM), a non-selective protein kinase inhibitor known to induce apoptosis, was used as a positive control. After 72 h, cell viability was determined using the CellTiter-Glo 2.0 kit (Promega) according to the instructions of the manufacturer. The luminescence signal was measured on the Safire 2 microplate reader (TECAN) with 1 s integration time.

Example 5—Microsome Stability

Microsomal metabolic stability of the compounds was measured in 0.5 mg/ml CD-1 mouse (Corning or Xenotech) or human liver microsomes (Corning) for 45 min at 37° C. in 0.1 M potassium phosphate buffer (pH 7.4) with 1.0 mM EDTA. The starting concentration of the compounds was 1 μM (0.2% MeCN). The reactions were initiated by the addition of NADPH to 2 mM, and samples were quenched with MeCN at 0, 5, 14, 30, 45 min. Linear regression of ln([compound]) versus time was used to determine the half-life, $t_{1/2}$. Testosterone was used for quality control.

Example 6—Compiled Data for Enzymatic Activity, Antiviral Activity, Cell Cytotoxicity, and Microsome Stability The data presented in the table below has been reproducible, and the 95% confidence intervals extracted from the fits of the data are overall: <±70% of the reported $K_i$ and $EC_{50}$ values.

TABLE 1

| Compound | $K_i$ Mpro-coil [nM] WT | $K_i$ Mpro-coil [nM] E166V | $K_i$ Mpro-coil fold-change E166V/WT | $EC_{50}$ SARS-CoV-2 [[μM] Huh 7.5.1++ | $EC_{50}$ SARS-CoV-2 [[μM] A549+ | $CC_{50}$ [μM] A549+ | Microsome stability $t_{1/2}$ [min] Human | Microsome stability $t_{1/2}$ [min] Mouse |
|---|---|---|---|---|---|---|---|---|
| (I-1) | 0.37 | 28 | 76 | 0.23 | 0.31 | >100 | 75 | 85 |
| (I-2) | 0.96 | 7.9 | 8.2 | 0.35 | 0.12 | >100 | 29 | 14 |
| (I-3) | 0.15 | 0.82 | 5.5 | 0.07 | 0.11 | >100 | 56 | 38 |
| (I-4) | 0.59 | 5.5 | 9.3 | 0.08 | 0.07 | >100 | 26 | 5 |
| (II-1) | 4.67 | 121 | 26 | 0.07 | 0.28 | >100 | 47 | 16 |
| Reference | 0.29 | 113 | 389 | 0.10 | 0.12 | >100 | 18 | 13 |

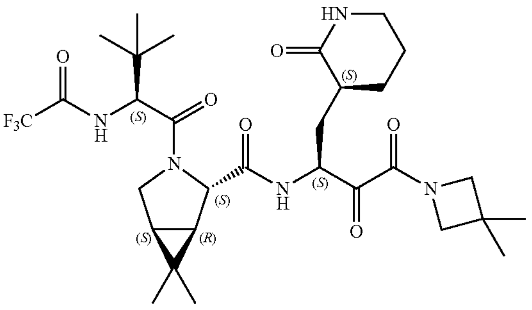

The foregoing examples are merely illustrative of embodiments of the disclosed processes described herein and are not intended to limit the disclosed methods. Variations and changes which are obvious to one skilled in the art are intended to be within the scope and nature of the disclosure which is defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing embodiments of the disclosure (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (for example, "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

What is claimed:

1. A compound having a structure of formula (I) or formula (II):

(I)

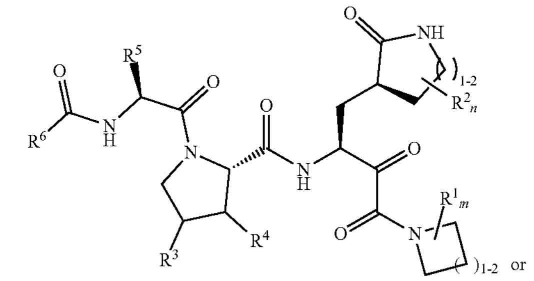

or (II)

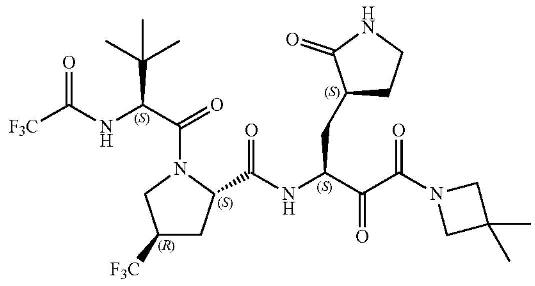

, or a pharmaceutically acceptable salt, solvate, or hydrate thereof, wherein $R^1$ and $R^2$ are each independently halo, $C_{1-3}$alkyl, or halo$C_{1-3}$alkyl;

m and n are each independently 0, 1, or 2;

$R^3$ and $R^4$ are each independently H, $C_{1-3}$alkyl, halo$C_{1-3}$ alkyl, or a 3 to 6-membered spiro ring optionally comprising 1 or 2 ring heteroatoms independently selected from N, O, and S, and the spiro ring is substituted with 0-2 $R^a$, or $R^3$ and $R^4$, taken together with the carbon atoms to which they are attached, form a $C_{3-6}$cycloalkyl substituted with 0-2 $R^a$;

each $R^a$ is independently halo, $C_{1-3}$alkyl, or halo$C_{1-3}$ alkyl;

$R^5$ is $C_{1-3}$alkyl, isobutyl, bridged bicyclo$C_{5-8}$alkyl, alkylene-$C_{3-8}$cycloalkyl, alkylene-$C_{1-4}$alkoxy, alkylene-O—$C_{3-8}$cycloalkyl wherein the cycloalkyl is optionally substituted with $C_{1-3}$alkyl; or $C_{3-8}$cycloalkyl optionally substituted with $C_{1-3}$alkyl, halo, halo$C_{1-4}$ alkyl, or $C_{1-3}$alkoxy; and $R^6$ is $C_{1-3}$alkyl, halo$C_{1-6}$alkyl, $C_{1-4}$alkoxy, $C_{3-6}$cycloalkoxy, or-haloalkylene-$C_{3-6}$cycloalkyl.

2. The compound according to claim 1, wherein

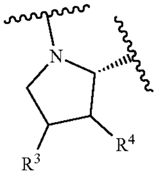

is selected from:

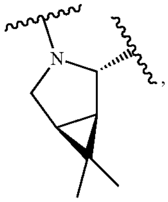,
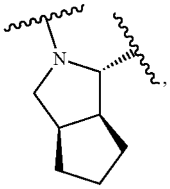,
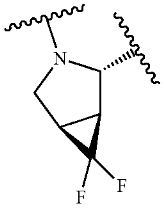,

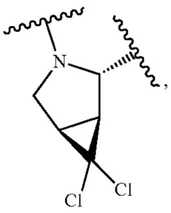,
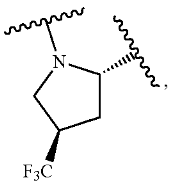, and

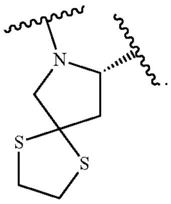.

3. The compound according to claim 2, wherein

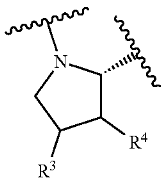

is:

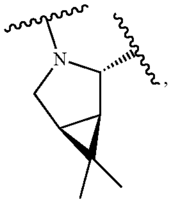, or 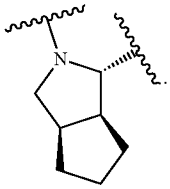.

4. The compound according to claim 3, wherein

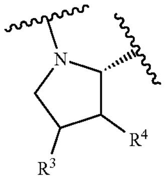

is:

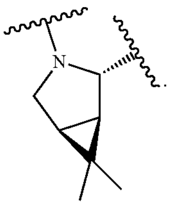 [SMILES: *[C@@H]1[C@@H]2[C@H](CN1*)C2(C)C].

5. The compound according to claim 1, characterized by formula (IA):

(IA)

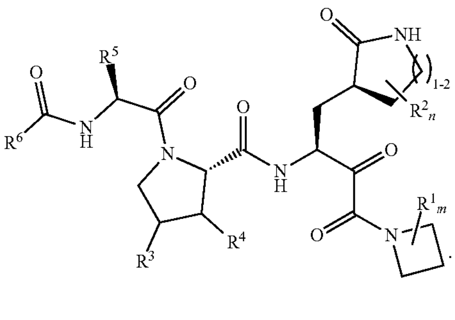.

6. The compound according to claim 5, characterized by formula (IB):

(IB)

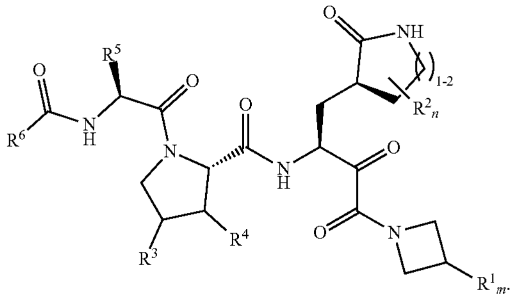

7. The compound according to claim 6, wherein m is 1 and $R^1$ is —F, —Cl, —Br, —$CH_3$, or —$CF_3$.

8. The compound according to claim 6, wherein m is 2 and

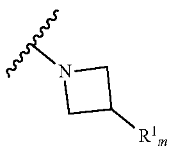

is

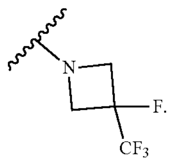

9. The compound according to claim 5, characterized by formula (IC) or (ID)

(IC)

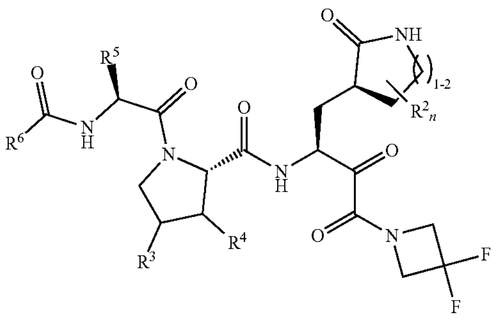

or

-continued (ID)

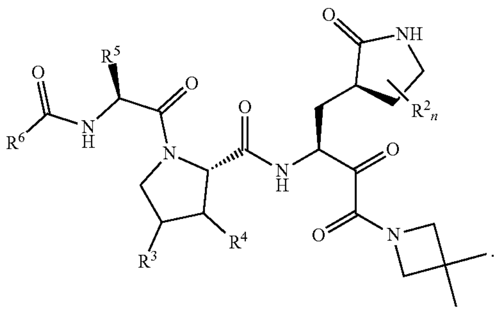

10. The compound according to claim 1, characterized by formula (IE):

(IE)

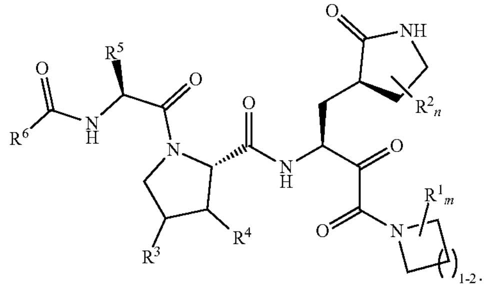

11. The compound according to claim 1, characterized by formula (IF):

(IF)

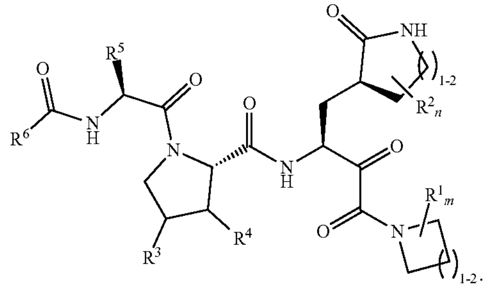

12. The compound according to claim 1, wherein $R^5$ is

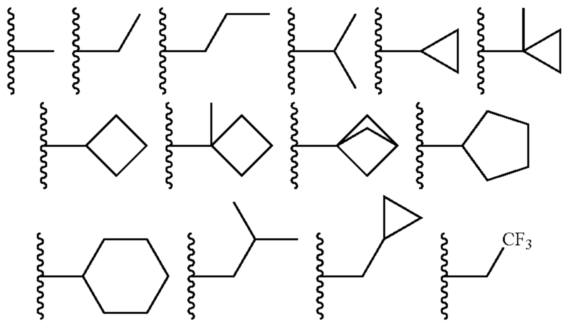

-continued

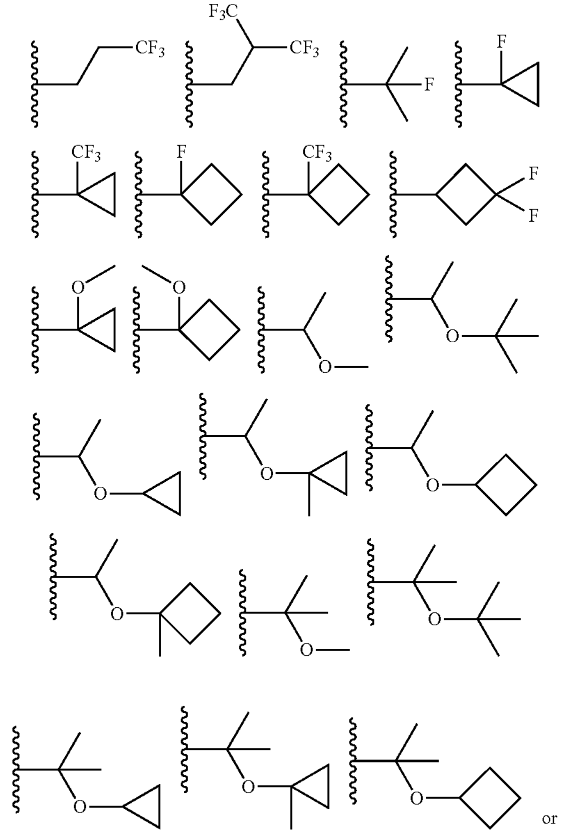

or

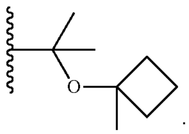

13. The compound according to claim 1, wherein $R^5$ is methyl, ethyl, 1-propyl, 2-propyl, cyclopropyl, cyclobutyl, cyclopentyl, cyclohexyl, isobutyl, or cyclopropyl-$CH_2$—.

14. The compound according to claim 13, wherein $R^5$ is 2-propyl.

15. The compound according to claim 13, wherein $R^5$ is cyclohexyl.

16. The compound according to claim 1, wherein $R^6$ is

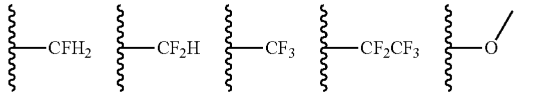

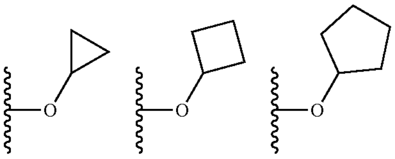

or

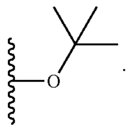

17. The compound according to claim 1, wherein $R^6$ is trifluoromethyl.

18. The compound according to claim 1, wherein $R^6$ is methoxy.

19. The compound according to claim 1 characterized by a structure selected from:

(I-1)

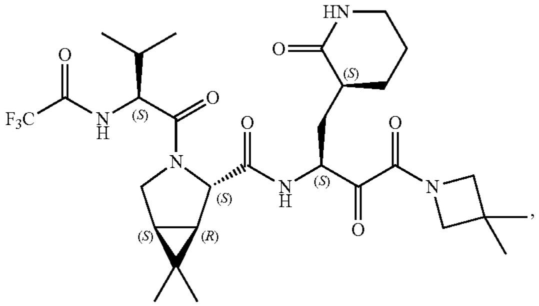

(I-2)

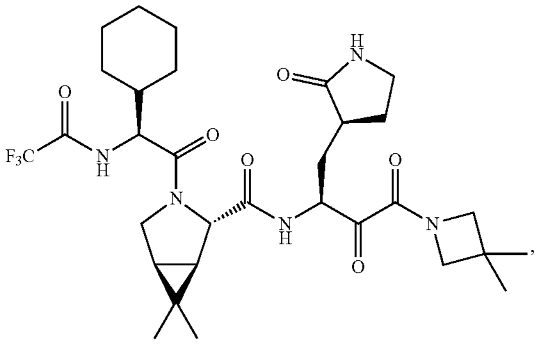

(I-3)

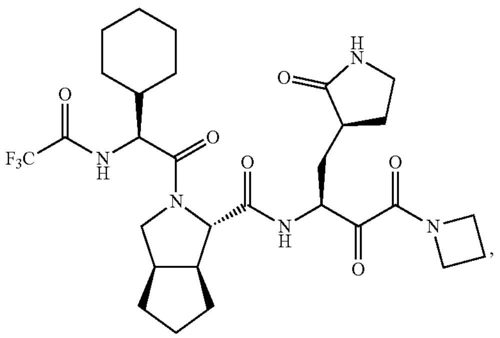

(I-4)

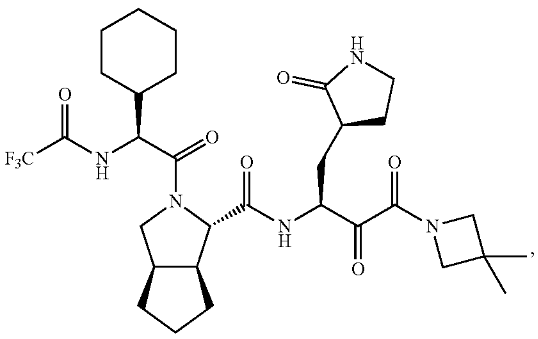

and

-continued (II)

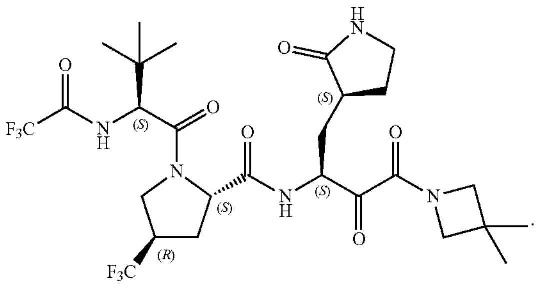

20. The compound of claim 19 having the structure of:

(I-1)

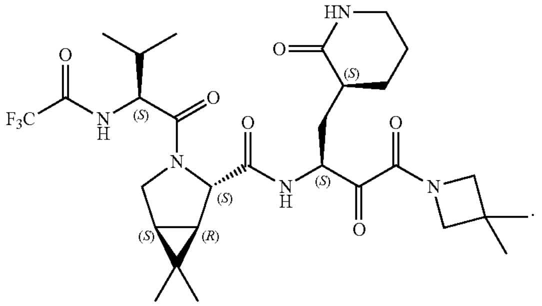

21. A pharmaceutical composition comprising the compound of claim 1 and a pharmaceutically acceptable carrier.

22. The pharmaceutical composition of claim 21, wherein the pharmaceutical composition is formulated for oral, parenteral, inhalational, intranasal, subcutaneous, intramuscular, or intravenous administration.

23. The pharmaceutical composition of claim 22, wherein the pharmaceutical composition is formulated for oral administration.

24. The pharmaceutical composition of claim 21, further comprising a second therapeutic agent used for treating a SARS-CoV-2 infection.

25. A method of treating or preventing a viral infection in an individual, comprising administering to an individual the therapeutically effective amount of the pharmaceutical composition of claim 21.

26. The method according to claim 25, wherein the viral infection is a coronavirus infection, norovirus infection, or enterovirus infection.

27. The method according to claim 26, wherein the coronavirus infection is a SARS-CoV-2 infection.

* * * * *